US012702268B2

(12) United States Patent
Korehisa et al.

(10) Patent No.: US 12,702,268 B2
(45) Date of Patent: Aug. 11, 2026

(54) ENDOSCOPIC SYSTEM, CONTROL METHOD, ENDOSCOPE CONTROL APPARATUS, AND PROGRAM

(71) Applicant: Sony Group Corporation, Tokyo (JP)

(72) Inventors: Makoto Korehisa, Kanagawa (JP); Shunsuke Hayashi, Kanagawa (JP)

(73) Assignee: SONY GROUP CORPORATION, Tokyo (JP)

(*) Notice: Subject to any disclaimer, the term of this patent is extended or adjusted under 35 U.S.C. 154(b) by 0 days.

(21) Appl. No.: 19/169,987

(22) Filed: Apr. 3, 2025

(65) Prior Publication Data

US 2025/0255458 A1 Aug. 14, 2025

Related U.S. Application Data

(63) Continuation of application No. 18/177,221, filed on Mar. 2, 2023, now abandoned, which is a
(Continued)

(30) Foreign Application Priority Data

Jul. 19, 2017 (JP) ................................ 2017-140081

(51) Int. Cl.
*G16H 40/63* (2018.01)
*A61B 1/00* (2006.01)
(Continued)

(52) U.S. Cl.
CPC ...... *A61B 1/00006* (2013.01); *A61B 1/00042* (2022.02); *A61B 1/307* (2013.01); *A61B 34/25* (2016.02); *G16H 40/63* (2018.01)

(58) Field of Classification Search
CPC . A61B 1/00006; A61B 1/00042; A61B 1/307; A61B 34/25; A61B 2017/00203;
(Continued)

(56) References Cited

U.S. PATENT DOCUMENTS 5,786,816 A 7/1998 Macrae et al.
6,485,413 B1 11/2002 Boppart et al.
(Continued)

FOREIGN PATENT DOCUMENTS

CN 206100249 U 4/2017
JP 2000-163269 A 6/2000
(Continued)

OTHER PUBLICATIONS

Vengalil (Self Deleting Executables, previously mailed on Dec. 2, 2022 in parent U.S. Appl. No. 16/629,969) (Year: 2010).*
(Continued)

*Primary Examiner* — Kambiz Abdi
*Assistant Examiner* — Tran N Nguyen
(74) *Attorney, Agent, or Firm* — XSENSUS LLP

(57) ABSTRACT

The present technology relates to a surgery system, a control method, a surgical apparatus, and a program that allow easy updating of a function of a medical apparatus. A configuration includes an information processor, and a surgical apparatus. The information processor includes a storage section storing an application, and a transmission section transmitting, in response to a request from the surgical apparatus, the application stored in the storage section. The surgical apparatus includes a reception section receiving the application transmitted by the transmission section, and an execution section executing the application received by the reception section.

20 Claims, 10 Drawing Sheets

Related U.S. Application Data continuation of application No. 16/629,969, filed as application No. PCT/JP2018/025471 on Jul. 5, 2018, now abandoned.

(51) Int. Cl.
*A61B 1/307* (2006.01)
*A61B 34/00* (2016.01)

(58) Field of Classification Search
CPC .......... A61B 2017/00207; A61B 2017/00973; A61B 2090/309; A61B 1/0002; A61B 90/361; A61B 2034/258; A61B 2090/365; A61B 1/00059; G16H 40/63; G16H 40/67; G16H 40/40; G06F 8/65; H04L 67/34
See application file for complete search history.

(56) References Cited

U.S. PATENT DOCUMENTS

| | | | | |
|---|---|---|---|---|
| 6,550,061 | B1 * | 4/2003 | Bearden | G06F 9/445 707/999.203 |
| 11,045,081 | B2 | 6/2021 | Matsumoto et al. | |
| 2003/0174205 | A1 | 9/2003 | Amling et al. | |
| 2004/0172302 | A1 * | 9/2004 | Martucci | A61B 5/4839 705/2 |
| 2005/0022274 | A1 | 1/2005 | Campbell et al. | |
| 2005/0097191 | A1 * | 5/2005 | Yamaki | G16H 40/63 709/219 |
| 2006/0281971 | A1 | 12/2006 | Sauer et al. | |
| 2007/0213790 | A1 | 9/2007 | Nolan et al. | |
| 2010/0228087 | A1 | 9/2010 | Shener | |
| 2012/0179670 | A1 | 7/2012 | Burke et al. | |
| 2013/0215213 | A1 | 8/2013 | Power et al. | |
| 2014/0184765 | A1 | 7/2014 | King | |
| 2014/0276950 | A1 | 9/2014 | Smaby et al. | |
| 2015/0243148 | A1 | 8/2015 | Faucette et al. | |
| 2015/0332196 | A1 | 11/2015 | Stiller et al. | |
| 2016/0015471 | A1 | 1/2016 | Piron et al. | |
| 2016/0140307 | A1 | 5/2016 | Brosnan et al. | |
| 2016/0154620 | A1 | 6/2016 | Tsuda et al. | |
| 2017/0020617 | A1 | 1/2017 | Weir et al. | |
| 2017/0068792 | A1 | 3/2017 | Reiner | |
| 2017/0172572 | A1 | 6/2017 | Collings et al. | |
| 2017/0209050 | A1 | 7/2017 | Fengler et al. | |
| 2017/0220769 | A1 | 8/2017 | Miller et al. | |
| 2018/0267291 | A1 | 9/2018 | Mikami et al. | |
| 2020/0360099 | A1 | 11/2020 | Smaby et al. | |

FOREIGN PATENT DOCUMENTS

| | | | |
|---|---|---|---|
| JP | 2003-256030 | A | 9/2003 |
| JP | 2007-313171 | A | 12/2007 |
| JP | 2010-191513 | A | 9/2010 |
| JP | 2012-024283 | A | 2/2012 |
| JP | 2016-209466 | A | 12/2016 |

OTHER PUBLICATIONS

Vengalil, Self Deleting Executables, 2010, https://www.codeproject.com/Articles/17052/Self-Deleting-Executables (Year: 2010).*
International Search Report and Written Opinion mailed on Aug. 21, 2018 for PCT/JP2018/025471 filed on Jul. 5, 2018, 9 pages including English Translation of the International Search Report.
Extended European Search Report issued May 12, 2020 in European Patent Application No. 18835993.9, 8 pages.
Garfinkel, Remembrance of data passed: a study of disk sanitization practices, 2003, in IEEE Security & Privacy, vol. 1, No. 1, pp. 17-27, Jan.-Feb. 2003.
Croft, Secure distribution of confidential information via self-destructing data, 2009 (Year: 2009).
Tilles, Writing Your Own Install and Uninstall Code, 2003, windows::developer Network (Year: 2003).

* cited by examiner

10
CCU
LIGHT SOURCE APPARATUS
ARM CONTROLLING APPARATUS
INPUTTING APPARATUS
TREATMENT TOOL CONTROLLING APPARATUS
PNEUMOPERITONEUM APPARATUS
RECORDER
PRINTER
20
21
23
30
31
33
35
37a
37b
37c
37d
40
41
43
45a
45b
45c
47a
47b
50
51
53
55
57
59
61
63
65
67
69
71
73
75

START SECOND PROCESSING BY MEDICAL APPARATUS
RECEIVE APPLICATION
S201
ACCEPT REQUEST TO EXECUTE APPLICATION
S202
EXECUTE APPLICATION
S203
SURGERY (EXAMINATION) FINISHED?
S204
NO
YES
DELETE APPLICATION
S205
END
START SECOND PROCESSING BY MONITORING APPARATUS
ACCEPT SELECTION OF FUNCTION AND CLINICAL DEPARTMENT
S231
SELECT APPLICATION
S232
TRANSMIT APPLICATION
S233
END

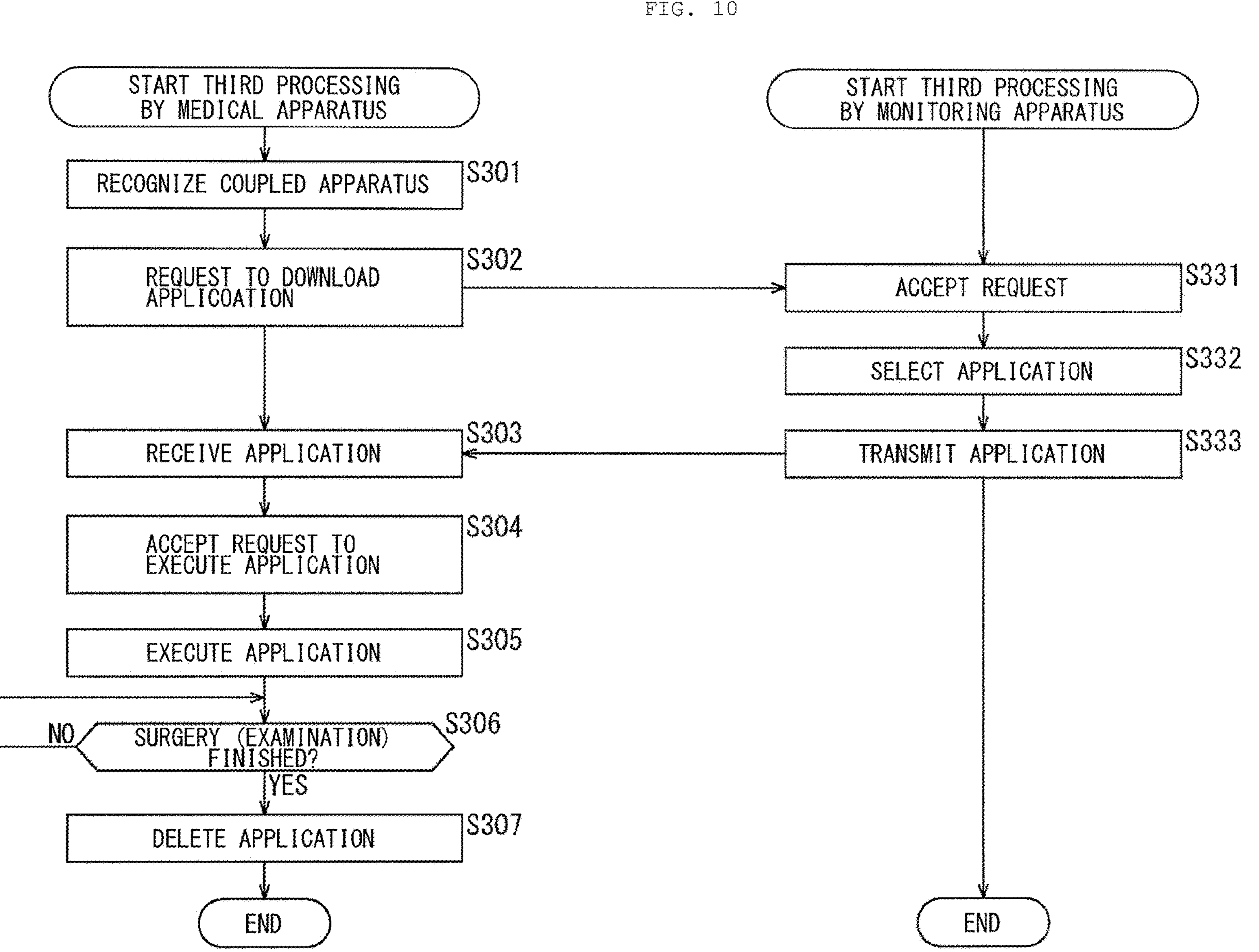
FIG. 10
START THIRD PROCESSING BY MEDICAL APPARATUS
RECOGNIZE COUPLED APPARATUS
S301
REQUEST TO DOWNLOAD APPLICOATION
S302
RECEIVE APPLICATION
S303
ACCEPT REQUEST TO EXECUTE APPLICATION
S304
EXECUTE APPLICATION
S305
SURGERY (EXAMINATION) FINISHED?
S306
NO
YES
DELETE APPLICATION
S307
END
START THIRD PROCESSING BY MONITORING APPARATUS
ACCEPT REQUEST
S331
SELECT APPLICATION
S332
TRANSMIT APPLICATION
S333
END

ENDOSCOPIC SYSTEM, CONTROL METHOD, ENDOSCOPE CONTROL APPARATUS, AND PROGRAM

CROSS-REFERENCE TO RELATED APPLICATIONS

The present application is a continuation of U.S. application Ser. No. 18/177,221, filed Mar. 2, 2023, which is a continuation of U.S. application Ser. No. 16/629,969, filed Jan. 10, 2020, which is based on PCT filing PCT/JP2018/025471, filed Jul. 5, 2018, which claims priority to JP 2017-140081, filed Jul. 19, 2017, the entire contents of each are incorporated herein by reference.

TECHNICAL FIELD

The present technology relates to a surgery system, a control method, a surgical apparatus, and a program, and relates to, for example, a surgery system, a control method, a surgical apparatus, and a program that allow easy updating of an application.

BACKGROUND ART

For a purpose of use at a medical site, for example, there have been proposed various techniques to generate, and display, an image synthesized by overlaying, on an ordinary image of an internal organ, etc. captured by an endoscopic surgery system, a special image indicating a location of a blood vessel or a lesion such as a tumor, which is difficult to recognize by the ordinary image.

For example, PTL 1 describes capturing an ordinary image and a special image by time sharing. In addition, for example, PTL 2 describes synthesizing an ordinary image and a special image and displaying the synthesized image.

CITATION LIST

Patent Literature

PTL 1: Japanese Unexamined Patent Application Publication No. 2007-313171

PTL 2: Japanese Unexamined Patent Application Publication No. 2012-24283

SUMMARY OF THE INVENTION

Problem to be Solved by the Invention

In a case of using an endoscopic surgery system in a surgery or examination, observation light used for capturing a special image, a method of image processing, etc. differ depending on a clinical department such as digestive surgery, urology, or otolaryngology. In addition, an efficient use of an operating room has become indispensable to a smooth operation of hospital management, and there is even a case of sharing one operating room among a plurality of clinical departments.

Installation of a plurality of medical apparatuses for respective clinical departments requires a storage area, and also requires an installation work for every use. In addition, there has been a possibility that incorporating applications for a plurality of clinical departments in one medical apparatus would cause an increase in storage region for application programs, complicate a structure inside the medical apparatus, and result in an increase in system cost and development expenditure.

Meanwhile, for example, an endoscopic surgery system is expected to be more useful, and is expected to allow updating of an application, etc. more reliably and more easily for better usability.

The present technology is considered in view of such a circumstance and makes it possible to perform updating of an application, etc. more reliably and more easily.

Means for Solving the Problem

A surgery system in an aspect of the present technology includes an information processor, and a surgical apparatus. The information processor includes a storage section storing an application, and a transmission section transmitting, in response to a request from the surgical apparatus, the application stored in the storage section. The surgical apparatus includes a reception section receiving the application transmitted by the transmission section, and an execution section executing the application received by the reception section.

A first control method in an aspect of the present technology, for a surgery system that includes an information processor and a surgical apparatus, includes: causing the information processor to store an application per clinical department, and transmit the stored application in response to a request from the surgical apparatus; and causing the surgical apparatus to receive the application transmitted by the information processor, and execute the received application.

A surgical apparatus in an aspect of the present technology includes an acquisition section that acquires an application per clinical department from an information processor that stores the application, and an execution section that executes the application acquired by the acquisition section.

A second control method in an aspect of the present technology includes acquiring an application per clinical department from an information processor that stores the application, and executing the acquired application to thereby execute processing suitable for the clinical department.

A program in an aspect of the present technology causes a computer, which controls a medical apparatus, to execute processing that includes: acquiring an application per clinical department from an information processor that stores the application; and executing the acquired application to thereby execute processing suitable for the clinical department.

In the surgery system and the first control method in an aspect of the present technology, the information processor transmits an application that is stored therein in response to a request from the surgical apparatus, and the surgical apparatus receives the application from the information processor and executes the received application.

In the surgical apparatus, the second control method, and the program in an aspect of the present technology, an application is acquired from the information processor that stores an application per clinical department, and the acquired application is executed.

It is to be noted that the surgical apparatus may be an independent apparatus or may be an internal block included in an apparatus.

In addition, it is possible to provide the program through transmission via a transmission medium or recording on a recording medium.

Effects of the Invention

According to an embodiment of the present technology, it is possible to perform updating of an application, etc. more reliably and more easily.

It is to be noted that the above-described effects are not necessarily limitative, and may be any of the effects described in the present disclosure.

BRIEF DESCRIPTION OF DRAWINGS

FIG. 10 describes processing by a system in a third embodiment.

MODES FOR CARRYING OUT THE INVENTION

In the following, modes to carry out the present technology (hereinafter, referred to as embodiments) are described.

<Configuration of Medical System>

Figure 1:
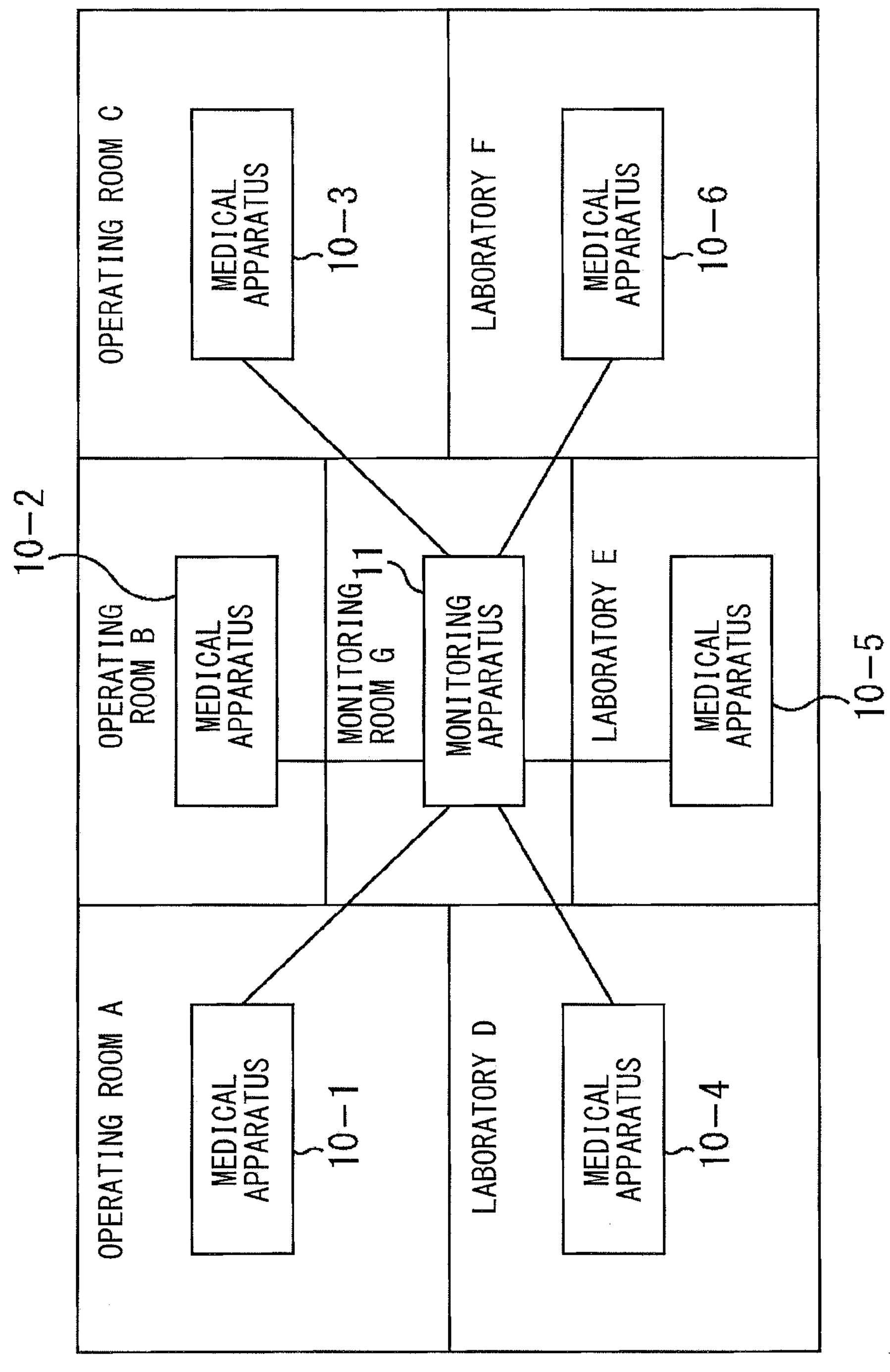
FIG. 1 illustrates a configuration of an embodiment of a medical system to which the present technology is applied.

The present technology is applicable to a medical system. As a medical system, for example, it is possible to assume a system having a configuration as illustrated in FIG. 1. FIG. 1 assumes a hospital, and illustrates a case where the hospital includes an operating room A, an operating room B, an operating room C, a laboratory D, a laboratory E, a laboratory F, and a monitoring room G.

A medical apparatus 10-1 is provided in the operating room A, a medical apparatus 10-2 is provided in the operating room B, and a medical apparatus 10-3 is provided in the operating room C. In addition, a medical apparatus 10-4 is provided in the laboratory D, a medical apparatus 10-5 is provided in the laboratory E, and a medical apparatus 10-6 is provided in the laboratory F. In addition, a monitoring apparatus 11 is provided in the monitoring room G.

The monitoring apparatus 11 and each of the medical apparatuses 10-1 to 10-6 are coupled to each other via a network to enable data transfer between each other. It is possible to configure the network using a wired or/and wireless LAN (Local Area Network).

As described later, for example, the medical apparatus 10-1 downloads an application managed by the monitoring apparatus 11 and executes processing on the basis of the application. In addition, here, the medical system is continuously described by exemplifying a case of including the medical apparatuses 10-1 to 10-6 and the monitoring apparatus 11, but the medical system is not limited to such a configuration. The medical system to which the present technology is applied is applicable to a configuration that includes at least one medical apparatus 10 and the monitoring apparatus 11.

The medical apparatuses 10-1 to 10-6 are each a surgical apparatus used in performing a surgery, or an examination apparatus used in performing an examination. In addition, for example, the medical apparatuses 10-1 to 10-6 are each a rigid endoscope that is an endoscope for a surgery, an endoscope for a diagnosis (including a flexible scope and a capsule type), an MRI (Magnetic Resonance Imaging), an ultrasonic diagnostic apparatus, etc. In the following description, in a case where it is not necessary to distinguish the medical apparatuses 10-1 to 10-6 from one another separately, the medical apparatuses 10-1 to 10-6 are simply referred to as the medical apparatus 10.

It is possible to configure the monitoring apparatus 11 with an information processor such as a personal computer (PC), and as described later, the monitoring apparatus 11 has a function to cause an application to be downloaded in response to a request from the medical apparatus 10, while having a function to manage the application.

<Configuration of Endoscopic Surgery System>

A configuration of an endoscope is described here as an example of the medical apparatus 10. Here, an endoscopic surgery system is described as an example, but the medical apparatus 10 is also applicable to a surgical operation system, a microsurgery system, and so on.

Figure 2:
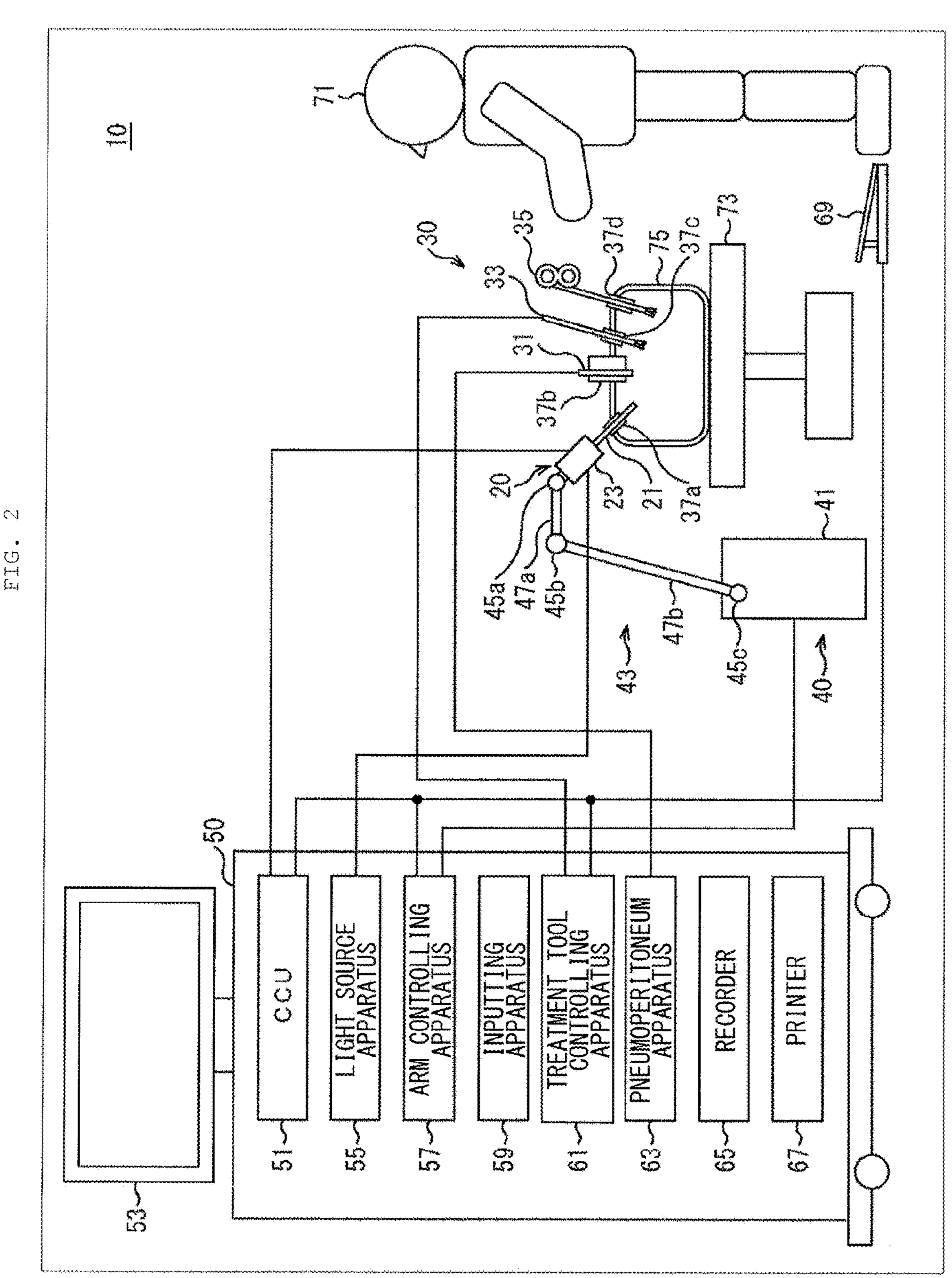
FIG. 2 illustrates a configuration of an embodiment of an endoscopic surgery system.

FIG. 2 illustrates an example of a schematic configuration of the endoscopic surgery system 10 to which a technique according to the present disclosure is applicable. FIG. 2 illustrates a state in which a surgeon (doctor) 71 is performing a surgery on a patient 75 on a patient bed 73, using the endoscopic surgery system 10. As illustrated, the endoscopic surgery system 10 includes an endoscope 20, another surgical instrument 30, a supporting arm apparatus 40 that supports the endoscope 20, and a cart 50 on which various apparatuses for an endoscopic surgery are mounted.

In the endoscopic surgery, instead of performing a laparotomy by cutting an abdominal wall, a plurality of tubular perforating instruments referred to as trocars 37*a* to 37*d* is pierced through the abdominal wall. Then, through the trocars 37*a* to 37*d*, a lens tube 21 of the endoscope 20, and other surgical instruments 30 are inserted into a body cavity of the patient 75. In the illustrated example, as other surgical instruments 30, a pneumoperitoneum tube 31, an energy treatment tool 33, and forceps 35 are inserted into the body cavity of the patient 75. In addition, the energy treatment tool 33 is a treatment tool with which to perform a tissue incision and an abrasion, or a blood vessel blockage, etc. by a high-frequency current or ultrasonic vibration. However, the surgical instrument 30 that is illustrated is a mere example, and as the surgical instrument 30, for example, various surgical instruments typically used for an endoscopic surgery such as tweezers or a retractor may be used.

An image of an operative site in the body cavity of the patient 75, which is captured by the endoscope 20, is displayed in a display apparatus 53. The surgeon 71, while looking at the image of the operative site displayed in the display apparatus 53 in real time, performs treatment, for example, excising an affected area using the energy treatment tool 33 and the forceps 35. It is to be noted that each of the pneumoperitoneum tube 31, the energy treatment tool 33, and the forceps 35 is supported by the surgeon 71, an assistant, or the like during a surgery.

(Supporting Arm Apparatus)

The supporting arm apparatus 40 includes an arm part 43 that extends from a base part 41. In the illustrated example, the arm part 43 includes joint parts 45*a*, 45*b*, and 45*c* and links 47*a* and 47*b*, and is driven by control from an arm controlling apparatus 57. The arm part 43 supports the endoscope 20 and controls a position and a posture thereof. This makes it possible to achieve fixing of a stable position of the endoscope 20.

(Endoscope)

The endoscope 20 includes the lens tube 21 having a predetermined length from an apical end being inserted into the body cavity of the patient 75, and the camera head 23 coupled to a base end of the lens tube 21. In the illustrated example, illustrated is the endoscope 20 configured as a so-called rigid scope that includes the lens tube 21 having rigidness, but the endoscope 20 may be configured as a so-called flexible scope that includes the lens tube 21 having flexibility.

The apical end of the lens tube 21 has an opening in which an objective lens is fitted. To the endoscope 20, a light source apparatus 55 is coupled, and light generated by the light source apparatus 55 is guided to the apical end of the lens tube by a light guide that extends across an inside of the lens tube 21, to be emitted to an observation target in the body cavity of the patient 75 via the objective lens. It is to be noted that the endoscope 20 may be a forward-viewing endoscope, or may be an oblique-viewing endoscope or a lateral-viewing endoscope.

Inside the camera head 23, an optical system and an imaging device are provided, and light reflected from the observation target (observation light) is collected into the imaging device by the optical system. The imaging device performs photoelectric conversion of the observation light, to generate an electric signal corresponding to the observation light, that is, an image signal corresponding to an observed image. The image signal is transmitted to a camera control unit (CCU: Camera Control Unit) 51 as raw data. It is to be noted that the camera head 23 has a function to adjust a magnification and a focal length by driving the optical system appropriately.

It is to be noted that for example, to correspond to stereopsis (3D or three-dimensional display), etc., the camera head 23 may include a plurality of imaging devices. In this case, inside the lens tube 21, a plurality of relay optical systems is provided each of which is intended to guide the observation light into a corresponding one of the plurality of imaging devices.

(Various Apparatuses Mounted on Cart)

The CCU 51 includes a CPU (Central Processing Unit) and a GPU (Graphics Processing Unit), and integrally controls an action of the endoscope 20 and the display apparatus 53. Specifically, the CCU 51 performs various types of image processing, for example, development processing (demosaicing) on an image signal received from the camera head 23 and displays an image on the basis of the image signal. The CCU 51 provides, to the display apparatus 53, the image signal on which the image processing is performed. In addition, the CCU 51 transmits a control signal to the camera head 23, to control driving thereof. The control signal may include information regarding an imaging condition such as a magnification or a focal length.

The display apparatus 53, in accordance with the control from the CCU 51, displays an image on the basis of the image signal on which image processing is performed by the CCU 51. For example, in a case where the endoscope 20 corresponds to high-resolution imaging such as 4K (horizontal pixel number 3840×vertical pixel number 2160) or 8K (horizontal pixel number 7680×vertical pixel number 4320), and/or in a case where the endoscope 20 corresponds to 3D display, in accordance with each of the cases, a corresponding one of the display apparatus 53 that enables high-resolution display and/or the display apparatus 53 that enables three-dimensional display may be used. In a case where the display apparatus 53 corresponds to high-resolution imaging such as 4K or 8K, using the display apparatus 53 having a size of 55 inches or larger makes it possible to obtain a stronger sense of immersion. In addition, a plurality of display apparatuses 53 having different resolutions and sizes may be provided in accordance with an intended use.

For example, the light source apparatus 55 includes a light source such as an LED (light emitting diode), and supplies the endoscope 20 with irradiation light that is used when imaging the operative site.

For example, the arm controlling apparatus 57 includes a processor such as a CPU, and operates in accordance with a predetermined program, thus controlling driving of the arm part 43 in the supporting arm apparatus 40 in accordance with a predetermined control method.

An inputting apparatus 59 is an input interface for the endoscopic surgery system 10. A user is able to perform input of various types of information and input of an instruction to the endoscopic surgery system 10 via the inputting apparatus 59. For example, via the inputting apparatus 59, the user inputs various types of information regarding a surgery such as physical information on a patient or information regarding a surgery technique. In addition, for example, via the inputting apparatus 59, the user inputs an instruction to drive the arm part 43, an instruction to change an imaging condition (such as a type of irradiation light, a magnification, or a focal length) for imaging by the endoscope 20, an instruction to drive the energy treatment tool 33, and so on.

A type of the inputting apparatus 59 is not limited, and the inputting apparatus 59 may be any type of known inputting apparatus. For example, as the inputting apparatus 59, a mouse, a keyboard, a touch panel, a switch, a foot switch 69 and/or a lever, etc. is applicable. In a case of using a touch panel as the inputting apparatus 59, the touch panel may be provided on a display surface of the display apparatus 53.

Alternatively, for example, the inputting apparatus 59 is a device worn by a user, such as an eyeglass-type wearable device or an HMD (Head Mounted Display), and various types of input are performed in accordance with a gesture or line of sight of the user that is detected by these devices. In addition, the inputting apparatus 59 includes a camera that is able to detect a motion of the user, and various types of input are performed in accordance with the gesture or line of sight of the user that is detected from a video captured by the camera.

Furthermore, the inputting apparatus 59 includes a microphone that is able to collect a voice of the user, and various types of input are performed by voice via the microphone. Thus, configuring the inputting apparatus 59 to allow input of various types of information in a non-contact manner particularly allows a user belonging to a clean area (for example, the surgeon 71) to manipulate an apparatus belonging to an unclean area in a non-contact manner. In addition, this also allows the user to manipulate the apparatus without releasing a hand from a surgical instrument that the user is holding, thus increasing user convenience.

A treatment tool controlling apparatus 61 controls driving of the energy treatment tool 33 that is used for tissue cauterization, incision, blood vessel blockage, and so on. To secure a visual field by the endoscope 20 as well as securing a workspace for the surgeon, a pneumoperitoneum apparatus 63 sends gas into the body cavity of the patient 75 through the pneumoperitoneum tube 31 to inflate the body cavity. A recorder 65 is an apparatus that is able to record various types of information regarding a surgery. A printer 67 is an apparatus that is able to print various types of information regarding a surgery in various formats such as text, an image, or a graph.

In the following, a particularly characteristic configuration in the endoscopic surgery system 10 is further described in detail.

(Supporting Arm Apparatus)

The supporting arm apparatus 40 includes the base part 41 that is a pedestal, and the arm part 43 that extends from the base part 41. In the illustrated example, the arm part 43 includes a plurality of joint parts 45*a*, 45*b*, and 45*c* and links 47*a* and 47*b* that are linked together by the joint 45*b*. However, FIG. 2 illustrates a simplified configuration of the arm part 43 for the sake of simplicity.

Actually, to allow the arm part 43 to have a desired degree of freedom, a shape, the number, and a position of each of the joint parts 45*a* to 45*c* and each of the links 47*a* and 47*b*, as well as a direction of a rotational axis of each of the joint parts 45*a* to 45*c*, and so on may be appropriately set. For example, the arm part 43 may be preferably configure to have a six or higher degrees of freedom. This allows the endoscope 20 to travel with freedom within a movable range of the arm part 43, thus making it possible to insert the lens tube 21 of the endoscope 20 into the body cavity of the patient 75 from a desired direction.

The joint parts 45*a* to 45*c* each include an actuator, and the joint parts 45*a* to 45*c* are each configured to be rotatable around a predetermined rotational axis when driven by the actuator. The arm controlling apparatus 57 controls driving of the actuator, which controls a rotation angle of each of the joint parts 45*a* to 45*c*, thus controlling the driving of the arm part 43. This makes it possible to achieve a control of the position and the posture of the endoscope 20. At this time, the arm controlling apparatus 57 is able to control the driving of the arm part 43 in accordance with various known control methods such as force control or position control.

For example, the surgeon 71 may appropriately perform manipulation input via the inputting apparatus 59 (including the foot switch 69), and thereby cause the arm controlling apparatus 57 to appropriately control the driving of the arm part 43 in accordance with the manipulation input, to control the position and the posture of the endoscope 20. The control allows the endoscope 20 at the apical end of the arm part 43 to travel from a given position to another given position, and then to support the endoscope 20 in a fixed manner at a position after the travel. It is to be noted that the arm part 43 may be manipulated by a so-called master-slave method. In this case, the arm part 43 may be remotely manipulated by a user via the inputting apparatus 59 that is provided at a place distant from the operating room.

In addition, in a case where force control is applied, the arm controlling apparatus 57 may perform so-called power assist control in which the arm controlling apparatus 57, in response to an external force from the user, drives the actuator in each of the joint parts 45*a* to 45*c*, to cause the arm part 43 to travel smoothly following the external force. When the user moves the arm part 43 while having direct contact with the arm part 43, this allows the user to move the arm part 43 with relatively small force. This accordingly makes it possible to move the endoscope 20 more intuitively and by easier manipulation, thus making it possible to increase user convenience.

Here, generally, in an endoscopic surgery, the endoscope 20 is supported by a doctor called a scopist. In contrast, using the supporting arm apparatus 40 makes it possible to securely fix the position of the endoscope 20 without depending on manpower, thus making it possible to stably obtain an image of the operative site and perform a surgery smoothly.

It is to be noted that the arm controlling apparatus 57 need not necessarily be provided on the cart 50. In addition, the arm controlling apparatus 57 need not necessarily be one apparatus. For example, the arm controlling apparatus 57 may be provided in each of the joint parts 45*a* to 45*c* in the arm part 43 in the supporting arm apparatus 40, and driving control of the arm part 43 may be achieved by a plurality of arm controlling apparatuses 57 working in cooperation with one another.

(Light Source Apparatus)

The light source apparatus 55 supplies irradiation light to the endoscope 20 when imaging an operative site. For example, the light source apparatus 55 is configured by a white light source that includes an LED, a laser light source, or a combination thereof. At this time, in a case where the white light source includes a combination of RGB, or red, green, and blue, laser light sources, it is possible to control an output intensity and an output timing of each color (each wavelength) with high accuracy, thus making it possible to adjust a white balance of the captured image in the light source apparatus 55.

In addition, in this case, it is also possible to irradiate the observation target with laser light from each of the RGB laser light sources by time division, and control driving of the imaging device in the camera head 23 in synchronization with the irradiation timing, thus capturing an image corresponding to each of RGB by time division. This method makes it possible to obtain a color image without providing the imaging device with a color filter.

In addition, driving of the light source apparatus 55 may be controlled to change intensity of outputted light at a predetermined time. Through obtaining an image by time division by controlling the driving of the imaging device in the camera head 23 in synchronization with a timing of the change in light intensity, and synthesizing the image, it is possible to generate a high dynamic range image without a so-called blocked up shadow or blown out highlight.

In addition, the light source apparatus 55 may be configured to be able to supply light having a predetermined wavelength bandwidth corresponding to a special light observation. In the special light observation, for example, a so-called narrow band light observation (Narrow Band Imaging) is performed. In the narrow band observation, light having a narrower bandwidth than the irradiation light (in other words, white light) in an ordinary observation is emitted utilizing a wavelength dependence of light absorption in a body tissue, thus imaging a predetermined tissue such as a blood vessel in a mucous membrane surface layer at a high contrast.

Alternatively, in the special light observation, a fluorescence observation that is to obtain an image by fluorescence generated by emitting excitation light may be performed. In the fluorescence observation, observation may be performed such as observing fluorescence from a body tissue by irradiating the body tissue with excitation light (self-fluorescence observation), or obtaining a fluorescent image by locally injecting a reagent such as indocyanine green (ICG)

into a body tissue while irradiating the body tissue with excitation light corresponding to a fluorescence wavelength of the reagent. The light source apparatus 55 may be configured to be able to supply narrow band light and/or excitation light that correspond to such a special light observation.

(Camera Head and CCU)

Figure 3:
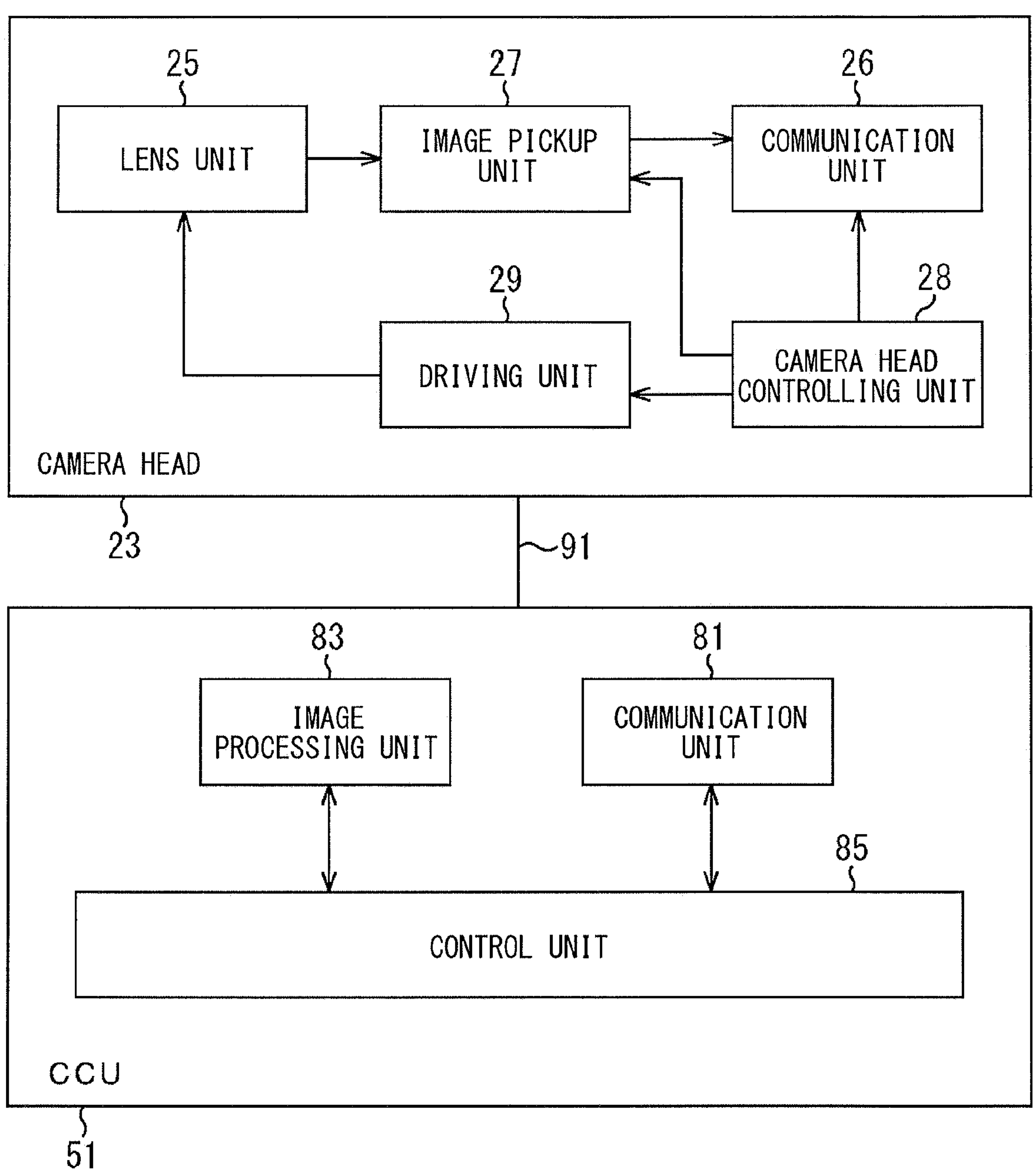
FIG. 3 is a block diagram that illustrates an example of a functional configuration of a camera head and a CCU.

With reference to FIG. 3, a function of each of the camera head 23 and the CCU 51 in the endoscope 20 is described in more detail. FIG. 3 is a block diagram that illustrates an example of a functional configuration of each of the camera head 23 and the CCU 51 that are illustrated in FIG. 2.

When referring to FIG. 3, the camera head 23 includes, as a function thereof, a lens unit 25, an image pickup unit 27, a driving unit 29, a communication unit 26, and a camera head controlling unit 28. In addition, the CCU 51 includes, as a function thereof, a communication unit 81, an image processing unit 83, and a control unit 85. The camera head 23 and the CCU 51 are coupled to each other by a transmission cable 91 to enable bidirectional communication.

First, the functional configuration of the camera head 23 is described. The lens unit 25 is an optical system provided at a part where the lens unit 25 is coupled to the lens tube 21. Observation light introduced through the apical end of the lens tube 21 is guided to the camera head 23, to enter the lens unit 25. The lens unit 25 is configured by a combination of a plurality of lenses including a zoom lens and a focus lens. The lens unit 25 has an optical characteristic adjusted to collect the observation light on a light receiving surface of the imaging device in the image pickup unit 27. In addition, the zoom lens and the focus lens are each configured to have a position movable on an optical axis to adjust the magnification and the focal point of a captured image.

The image pickup unit 27 includes an imaging device, and is disposed in a subsequent stage of the lens unit 25. Observation light transmitted through the lens unit 25 is collected on the light receiving surface of the imaging device, and an image signal corresponding to an observed image is generated by photoelectric conversion. The image signal generated by the image pickup unit 27 is provided to the communication unit 26.

As the imaging device included in the image pickup unit 27, for example, a CMOS (Complementary Metal Oxide Semiconductor) type imaging sensor is used that has a Bayer array and enables color imaging. It is to be noted that as the imaging device, for example, an imaging device may be used that is compatible with capturing of a high-resolution image of 4K or higher. Obtaining a high-resolution image of the operative site allows the surgeon 71 to grasp a state of the operative site in more detail, thus making it possible to operate the surgery more smoothly.

In addition, the imaging device included in the image pickup unit 27 includes a pair of imaging devices each of which is intended to obtain, for a corresponding one of a right eye and a left eye, an image signal that corresponds to a 3D display. Performing the 3D display allows the surgeon 71 to grasp a depth of a body tissue in the operative site more accurately. It is to be noted that in a case of the image pickup unit 27 having a multi-plate configuration, a plurality of systems of the lens unit 25 is provided in a manner corresponding to respective imaging devices.

In addition, the image pickup unit 27 need not necessarily be provided in the camera head 23. For example, the image pickup unit 27 may be provided immediately behind the objective lens, inside the lens tube 21.

The driving unit 29 includes an actuator and, in accordance with the control from the camera head controlling unit 28, causes the zoom lens and the focus lens in the lens unit 25 to travel along an optical axis by a predetermined distance. This makes it possible to appropriately adjust the magnification and the focal point of an image captured by the image pickup unit 27.

The communication unit 26 includes a communication device intended to transmit and receive various types of information to and from the CCU 51. The communication unit 26 transmits, as the raw data, an image signal obtained from the image pickup unit 27 to the CCU 51 via the transmission cable 91. At this time, to display the captured image of the operative site with a low latency, it is preferable that the image signal be transmitted by optical communication.

One reason for this is that, upon surgery, the surgeon 71 performs a surgery while observing a state of an affected area in accordance with the captured image, which requires a moving image of the operative site to be displayed as close to real time as possible. In a case of performing optical communication, the communication unit 26 includes a photoelectric conversion module that converts an electric signal into an optical signal. The image signal is converted into an optical signal by the photoelectric conversion module and then transmitted to the CCU 51 via the transmission cable 91.

In addition, the communication unit 26 receives, from the CCU 51, a control signal to control driving of the camera head 23. For example, the control signal includes information regarding an imaging condition, such as information specifying a frame rate for the captured image, information specifying an exposure value at the time of imaging, and/or information specifying the magnification and the focal point of the captured image. The communication unit 26 provides the received control signal to the camera head controlling unit 28.

It is to be noted that the control signal form the CCU 51 may also be transmitted by optical communication. In this case, the communication unit 26 includes a photoelectric conversion module that converts an optical signal into an electric signal, and the control signal is converted into an electric signal by the photoelectric conversion module and then provided to the camera head controlling unit 28.

It is to be noted that the above-described imaging condition, such as the frame rate, the exposure value, the magnification, or the focal point, is automatically set by the control unit 85 in the CCU 51 on the basis of the obtained image signal. In other words, the endoscope 20 has a so-called AE (Auto Exposure) function, an AF (Auto Focus) function, and an AWB (Auto White Balance) function.

The camera head controlling unit 28 controls the driving of the camera head 23 on the basis of the control signal received from the CCU 51 via the communication unit 26. For example, the camera head controlling unit 28 controls the driving of the imaging device in the image pickup unit 27 on the basis of the information specifying the frame rate of the captured image and/or the information specifying an exposure at the time of imaging. In addition, for example, on the basis of the information specifying the magnification and the focal point of the captured image, the camera head controlling unit 28 causes, via the driving unit 29, the zoom lens and the focus lens in the lens unit 25 to travel appropriately. The camera head controlling unit 28 may further have a function to store information for identifying the lens tube 21 and the camera head 23.

It is to be noted that disposing a configuration such as the lens unit 25 or the image pickup unit 27 in a sealing structure having a high airtightness and waterproof property allows the camera head 23 to have a tolerance to an autoclave sterilization treatment.

Next, the functional configuration of the CCU 51 is described. The communication unit 81 includes a communication device intended to transmit and receive various types of information to and from the camera head 23. The communication unit 81 receives an image signal transmitted from the camera head 23 via the transmission cable 91. At this time, as described above, the image signal may be preferably transmitted by optical communication. In this case, in a manner corresponding to the optical communication, the communication unit 81 includes a photoelectric conversion module that converts an optical signal into an electric signal. The communication unit 81 provides the image processing unit 83 with the image signal converted into the electric signal.

In addition, the communication unit 81 transmits, to the camera head 23, a control signal to control the driving of the camera head 23. The control signal may also be transmitted by optical communication.

The image processing unit 83 performs various types of image processing on an image signal that is the raw data transmitted from the camera head 23. Examples of the image processing include various types of known signal processing development processing, image-quality enhancement processing (including band-emphasis processing, super-resolution processing, NR (noise reduction) processing, and/or camera-shake correction processing), and/or enlargement processing (electronic zoom processing). In addition, the image processing unit 83 performs detection processing on the image signal to perform AE, AF, and AWB.

The image processing unit 83 includes a processor such as a CPU or a GPU, and the processor operates in accordance with a predetermined program, thus making it possible to perform the above-described image processing and detection processing. It is to be noted that in a case where the image processing unit 83 includes a plurality of GPUs, the image processing unit 83 appropriately divides information regarding the image signal, to cause the plurality of GPUs to perform image processing in parallel.

The control unit 85 performs various types of control regarding imaging of an operative site by the endoscope 20 and display of the captured image. For example, the control unit 85 generates a control signal to control the driving of the camera head 23. At this time, in a case where an imaging condition is inputted by a user, the control unit 85 generates a control signal on the basis of the input by the user. Alternatively, in a case where the endoscope 20 has the AE function, the AF function, and the AWB function, the control unit 85 appropriately calculates, in accordance with a result of the detection processing by the image processing unit 83, the exposure value, the focal length, and the white balance at an optimum level, to generate the control signal.

In addition, the control unit 85 causes the display apparatus 53 to display an image of the operative site on the basis of the image signal on which image processing is performed by the image processing unit 83. At this time, the control unit 85 recognizes various objects in the image of the operative site using various image recognition techniques.

For example, the control unit 85 detects an edge shape, a color, etc. of an object included in the image of the operative site, thus making it possible to recognize a surgical instrument such as forceps, a specific body site, bleeding, mist at the time of using the energy treatment tool 33, etc. When causing the display apparatus 53 to display the image of the operative site, the control unit 85 uses results of the recognition to display various types of surgery support information to be superimposed on an image of the operative site. The surgery support information, which is superimposed and displayed, is presented to the surgeon 71, thus making it possible to operate a surgery more safely and reliably.

The transmission cable 91 that couples the camera head 23 and the CCU 51 to each other is an electric signal cable corresponding to electric-signal communication, an optical fiber corresponding to optical communication, or a composite cable thereof.

Here, in the illustrated example, wired communication is performed using the transmission cable 91, but communication between the camera head 23 and the CCU 51 may also be performed wirelessly. In a case where wireless communication is performed therebetween, it is not necessary to install the transmission cable 91 in the operating room, and thus it may be possible to resolve a situation where movement of medical staff in the operating room is hampered by the transmission cable 91.

The example of the endoscopic surgery system 10 to which the technology according to the present disclosure is applicable has been described above.

It is to be noted that the endoscopic surgery system 10 has been described here as an example, but a system to which the technology according to the present disclosure is applicable is not limited to such an example. For example, the technology according to the present disclosure may also be applied to a flexible endoscopic surgery system for examination or a microsurgery system.

<Configuration of Medical Apparatus>

With reference to FIGS. 2 and 3, the specific configuration of the medical apparatus 10 has been described by exemplifying a case where the medical apparatus 10 is an endoscopic surgery system. Next, a function of the medical apparatus 10 is further described.

Figure 4:
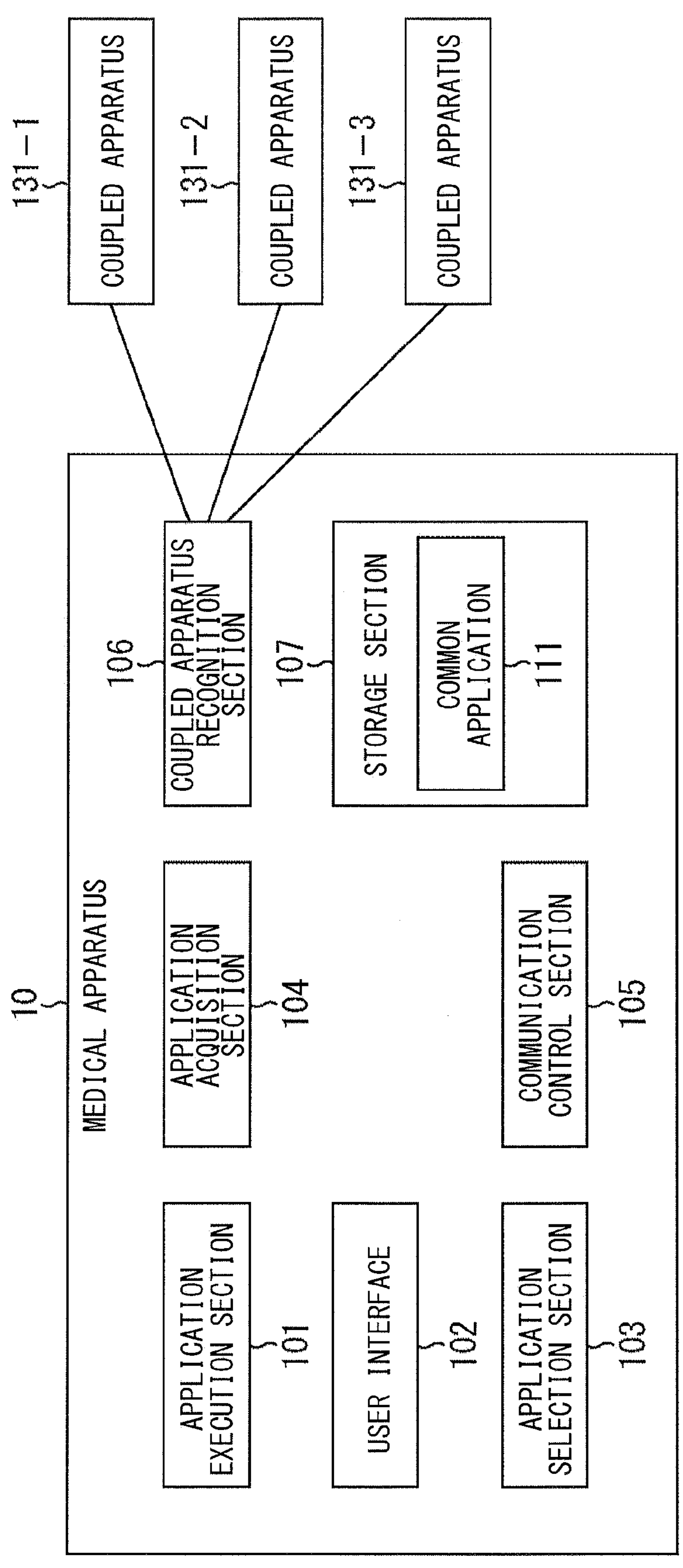
FIG. 4 describes a function of a medical apparatus.

The medical apparatus 10 illustrated in FIG. 4 includes an application execution section 101, a user interface 102, an application selection section 103, an application acquisition section 104, a communication control section 105, a coupled apparatus recognition section 106, and a storage section 107. In addition, the storage section 107 stores a common application 111.

The coupled apparatus recognition section 106 recognizes, from among coupled apparatuses 131-1 to 131-3 each having a possibility of being coupled to the medical apparatus 10, which one of the coupled apparatuses has been coupled. For example, the coupled apparatuses 131-1 to 131-3 may be each an apparatus including an imaging unit that images an affected area, or an apparatus including an imaging unit that images an examination site.

For example, the CCU 51 in the endoscopic surgery system 10 illustrated in FIGS. 2 and 3 is allowed to have the function of the medical apparatus 10 illustrated in FIG. 4.

The medical apparatus 10, for example, the endoscopic surgery system 10 is used for a surgery, an examination, etc. of various organs. The endoscopic surgery system 10 is a rigid endoscope that is an endoscope for a surgery, a flexible endoscope that is an endoscope for an examination, a capsule endoscope, and so on. In addition, examples of types of endoscope include a brain scope, an otolaryngological scope, a thoracoscope, a bronchoscope, a laparoscope, an enteroscope, a ureteroscope, a hysteroscope, and so on. Examples of an apparatus having a possibility of being coupled to the medical apparatus 10 as the coupled apparatus 131 may include these endoscopes, for example, the brain scope, and the otolaryngological scope.

In other words, the medical apparatus 10, for example, the CCU 51 may be a shared part, which is to be used, by the coupled apparatus 131 that is to be coupled to the medical apparatus 10, as a medical apparatus that performs an examination or surgery in brain, or used as a medical apparatus that performs an examination or surgery on ear, nose, and throat.

Thus, a target (organ) or a purpose (such as an examination purpose or a surgery purpose) differs depending on the coupled apparatus 131 that is to be coupled to the medical apparatus 10, and the coupled apparatus 131 suitable for the target and the purpose is selected and coupled.

The coupled apparatus recognition section 106 recognizes the coupled apparatus 131 that has been coupled. In accordance with a result of this recognition, it is determined what the medical apparatus 10 is intended for and what purpose the medical apparatus 10 is used for. Although described later, this determination is performed in any one of the coupled apparatus recognition section 106, the application selection section 103, the application acquisition section 104, and the monitoring apparatus 11, or in a plurality of these.

For example, when the coupled apparatus 131 that has been coupled is a brain scope, information that the coupled apparatus 131 is used for an examination or surgery in brain is acquired. Then, in this case, on the basis of this information, an application corresponding to an examination or surgery to be performed using the brain scope is supplied from the monitoring apparatus 11 to the medical apparatus 10.

The application acquisition section 104 acquires an application corresponding to the coupled apparatus 131 from the monitoring apparatus 11 (FIG. 1). For example, in a case where the coupled apparatus 131 is a brain scope, an application to cause the medical apparatus 10 to function as an apparatus that performs an examination or surgery in brain is acquired.

The application execution section 101 executes the application acquired by the application acquisition section 104, thus causing the medical apparatus 10 to execute processing based on the application. For example, in a case where the acquired application is an application for an examination or surgery in brain, the application execution section 101 executes the application, thus causing the medical apparatus 10 to function as an apparatus that performs image processing, etc. suitable for the examination or surgery in brain.

Processing that is executed as a result of the coupled apparatus recognition section 106 recognizing the coupled apparatus 131 is described later as a third embodiment. It is to be noted that in a case where processing is performed on the basis of a first embodiment or a second embodiment as described in the following, a configuration may eliminate the coupled apparatus recognition section 106 from the medical apparatus 10.

Although described in detail later, in the first or the second embodiment, an interface provided to a user through the user interface 102 is used, and in accordance with an option selected by the user, the application selection section 103 selects an application, and the application acquisition section 104 acquires the application selected by the application selection section 103.

It is assumed that the user interface 102 has a function to provide a user interface, and has a configuration including an apparatus that outputs an image or voice such as a display or a speaker, and an apparatus through which to input an instruction from a user such as a touch panel, a keyboard, and a mouse. For example, the user interface 102 has a configuration that allows the user to select a desired option from options displayed in the display.

The application execution section 101 executes an application that is acquired by the application acquisition section 104 or acquired as a result of the communication control section 105 performing control on communication with the monitoring apparatus 11 via a network. For example, in a case where the application execution section 101 uses a Linux (registered trademark) OS, i.e., operating system, the application is executed as a result of being added to a program that is dynamically executed using a function dlopen.

In addition, in a case where the application execution section 101 has a Web function, the application execution section 101 executes an application on a browser, or executes an application using java (registered trademark).

The application (application program) that is enabled for execution may be executed after an execution instruction from a user is accepted, or may be executed, even without any execution instruction from the user, when a predetermined trigger occurs.

The storage section 107 stores the common application 111. The common application 111 is an application shared by each medical apparatus 10. For example, execution of the common application 111 executes basic signal processing to display a surgery image (examination image), displays an option, or executes downloading of an application.

The medical apparatus 10 downloads an application from the monitoring apparatus 11, thus functioning as an apparatus that performs an examination or surgery in brain, or functioning as an apparatus that performs an examination or surgery on ear, nose, and throat. In the present embodiment, the monitoring apparatus 11 manages an application per clinical department, and the medical apparatus 10 downloads an application corresponding to a desired clinical department from the monitoring apparatus 11, to be used as the medical apparatus 10 that is able to perform processing corresponding to the clinical department.

<Configuration of Monitor>

A function of the monitoring apparatus 11 that manages an application per clinical department in this manner is described with reference to FIG. 5.

Figure 5:
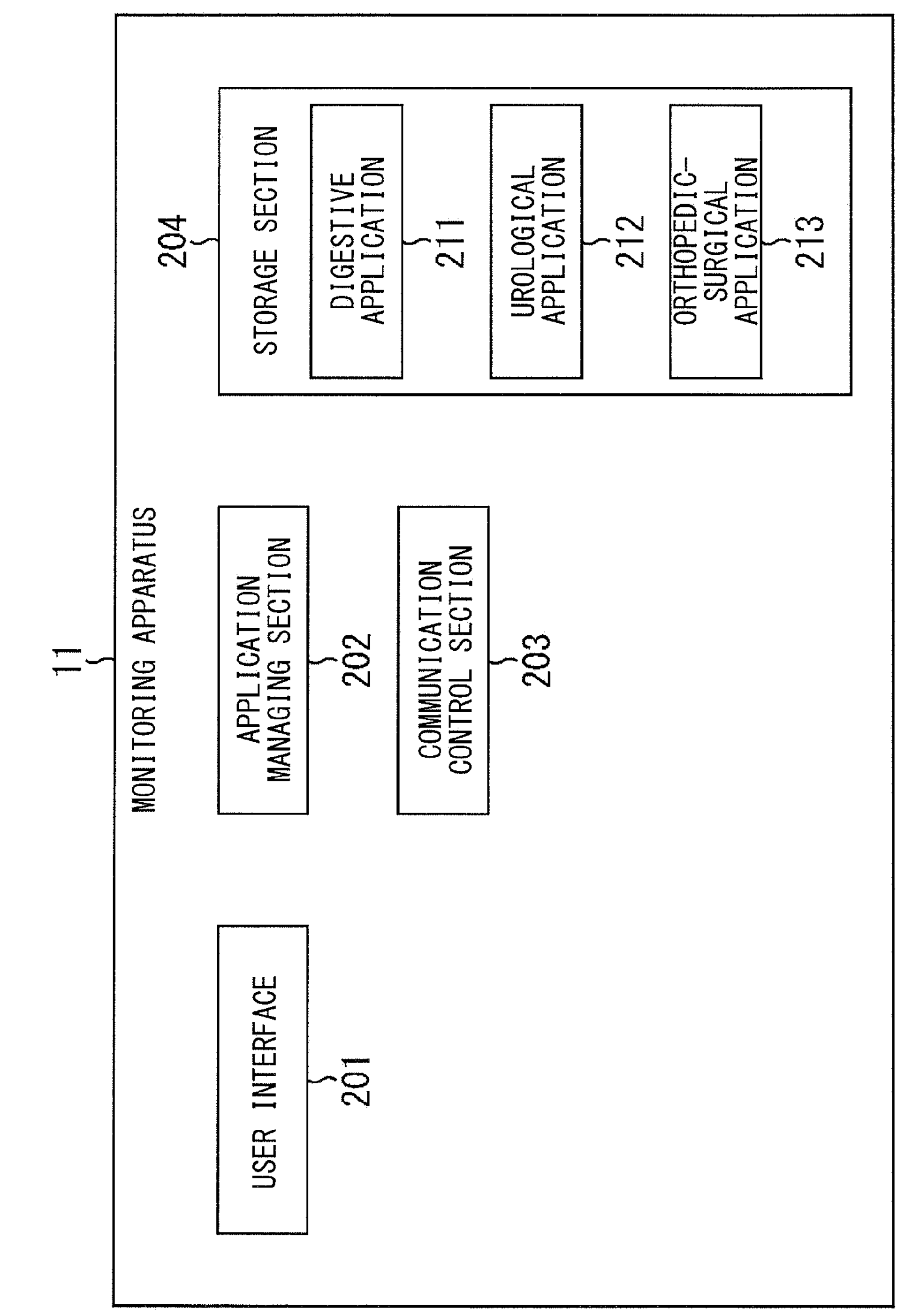
FIG. 5 describing a function of a monitoring apparatus.

As illustrated in FIG. 5, the monitoring apparatus 11 includes a user interface 201, an application managing section 202, a communication control section 203, and a storage section 204. In addition, the storage section 204 stores a digestive application 211, a urological application 212, and an orthopedic-surgical application 213.

As illustrated in FIG. 1, the monitoring apparatus 11 is provided in the monitoring room G, and has a configuration that enables, via a network, transmission and reception of an application or data transfer to and from each of the medical apparatuses 10-1 to 10-6.

Here, the monitoring apparatus 11 is continuously described assuming that the monitoring apparatus 11 is provided in the monitoring room G, but the monitoring apparatus 11 may be provided in a room other than the monitoring room G. In addition, the monitoring room G is a room provided for monitoring a surgery or examination that is performed in each of the operating rooms A to C or in each of the laboratories D to F. In the monitoring room G, an observer is present, and the observer monitors a surgery or examination.

In the second embodiment described later, description is given by exemplifying a case where the monitoring apparatus 11 is provided in the monitoring room G and an observer monitors a surgery or examination in this manner.

In the first and the third embodiments, it is sufficient that the monitoring apparatus 11 is coupled to enable communication with the medical apparatuses 10-1 to 10-6 as a server, and the monitoring apparatus 11 may be provided at any place. In other words, the monitoring apparatus 11 may be provided in any room other than the monitoring room G.

When referring to FIG. 5, the user interface 201 in the monitoring apparatus 11 has a function to accept a manipulation from a user. For example, it is assumed that the interface 201 has a configuration that includes a display including a touch panel. It is to be noted that as in the first or the second embodiment described later, in a case of providing the monitoring apparatus 11 as a server, it is also possible to assume the monitoring apparatus 11 having a configuration from which the user interface 201 is eliminated.

The application managing section 202 manages an application stored in the storage section 204. The storage section 204 stores the digestive application 211, the urological application 212, and the orthopedic-surgical application 213. When receiving, from the medical apparatus 10, a request to download an application, the application managing section 202 reads, from the storage section 204, an application that meets the request and transmits the application to the medical apparatus 10 under a control of the communication control section 203.

For example, when the medical apparatus 10 is used as an apparatus that performs a digestive examination or surgery, the application managing section 202 reads the digestive application 211 from the storage section 204, and transmits the digestive application 211 to the medical apparatus 10 via the communication control section 203.

Although the storage section 204 is continuously described assuming that the digestive application 211, the urological application 212, and the orthopedic-surgical application 213 are stored therein, this description is merely an example.

In other words, the storage section 204 also stores another application, for example, an application for another clinical department such as a brain-surgical application or an orthopedic-surgical application. Thus, the storage section 204 stores an application per clinical department.

The digestive application 211 is an application downloaded by the medical apparatus 10 when using the medical apparatus 10 as an apparatus to perform a digestive examination or surgery, and is an application intended to enable performance of processing specialized in a digestive examination or surgery.

The same applies to another application, and the urological application 212 is an application specialized in performing a urological examination or surgery, and the orthopedic-surgical application 213 is an application specialized in performing an examination or surgery related to orthopedic surgery.

Additional description is given of processing executed in a medical system that includes the monitoring apparatus 11 and the medical apparatus 10 each having such a configuration.

Processing in First Embodiment

Figure 6:
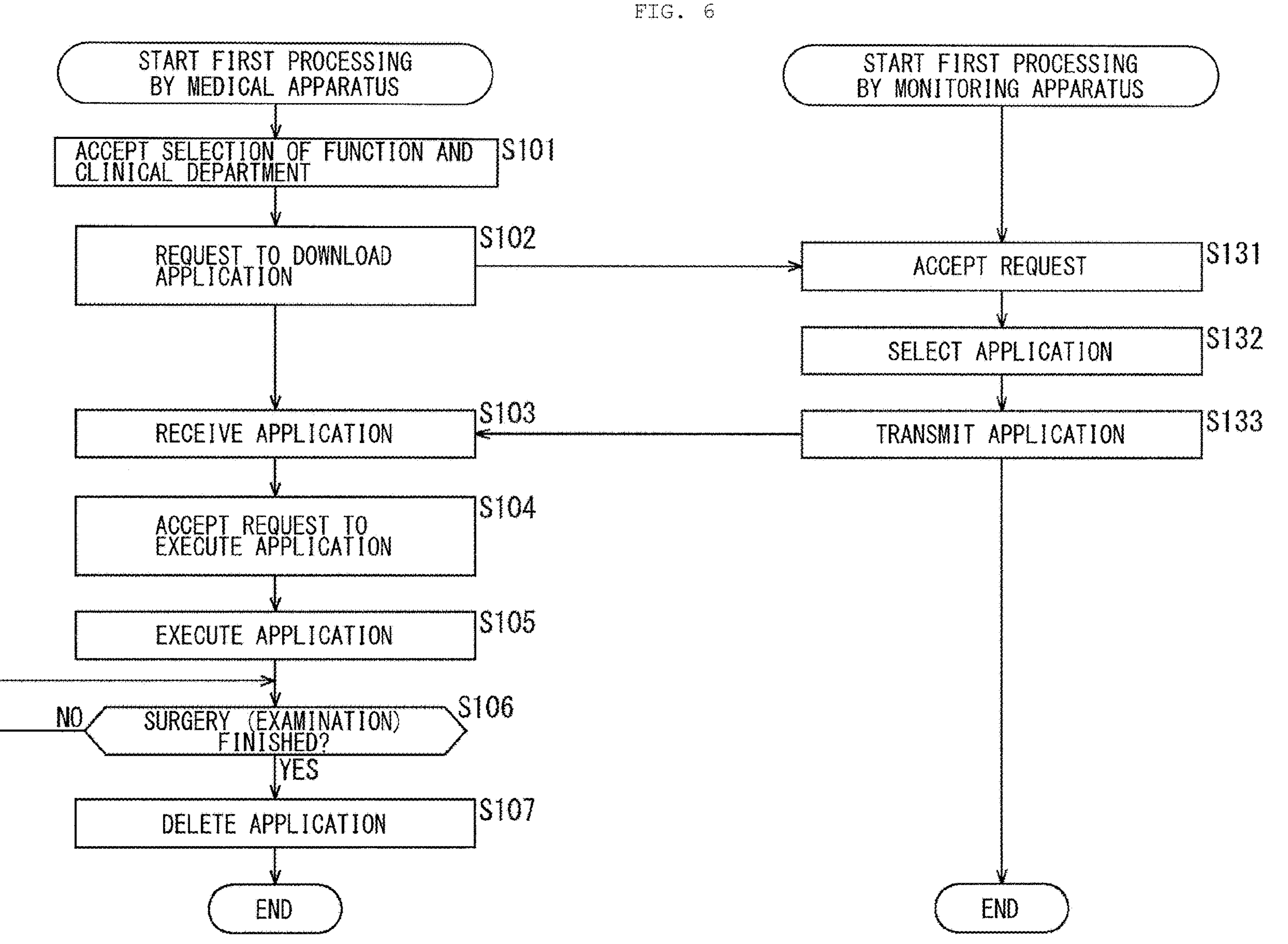
FIG. 6 describes processing by a system according to a first embodiment.

FIG. 6 is a flowchart that describes processing by a medical system in the first embodiment. The processing based on the flowchart illustrated in FIG. 6 is started after a medical apparatus is powered on.

In Step S101, the medical apparatus 10 accepts a selection of a function to use and a clinical department. For example, in Step S101, an option as illustrated in FIG. 7 is displayed on a display 301 included in the user interface 102 (FIG. 4) in the medical apparatus 10, and a user selects a desired option, and thereby the selection of the function to use is accepted.

Figure 7:
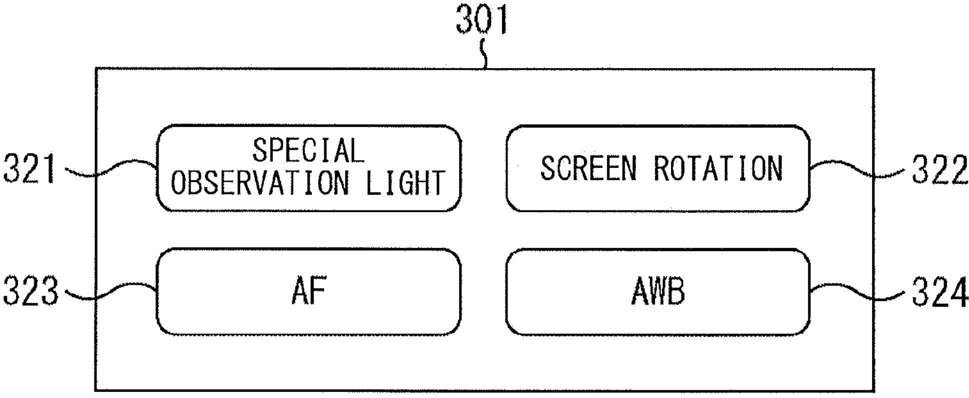
FIG. 7 illustrates an example of a screen displayed in a display.

When referring to FIG. 7, the display 301 displays an option 321 that is "special observation light", an option 322 that is "screen rotation", an option 323 that is "AF", and an option 324 that is "AWB". The option 321 that is "observation light" is an option selected when performing observation with special observation light. The option 322 that is "screen rotation" is an option selected when rotating a screen.

The option 323 that is "AF" is an option selected when turning autofocus (Autofocus) on or off. The option 324 that is "AWB" is an option selected when tuning color adjustment on or off in auto white balance (Auto White Balance).

The display 301 may display an option other than these options, or the display 301 may display these options together with the option other than these options.

An option regarding the function as illustrated in FIG. 7 may be displayed to allow a user (surgeon) to select a desired function. In addition, an option regarding the clinical department as illustrated in FIG. 8 may be displayed to allow the user (surgeon) to select a desired clinical department.

Figure 8:
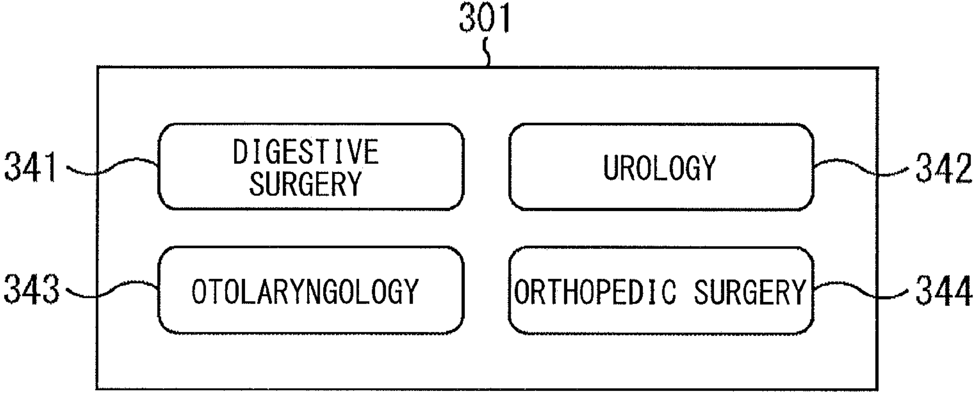
FIG. 8 illustrates another example of the screen displayed in the display.

When referring to FIG. 8, in the example of a display illustrated in FIG. 8, the display 301 displays an option 341 that is "digestive surgery", an option 342 that is "urology", an option 343 that is "otolaryngology", and an option 344 that is "orthopedic surgery".

The option 341 that is "digestive surgery" is an option selected when performing a digestive examination or surgery. The option 342 that is "urology" is an option selected when performing a urological examination or surgery.

The option 343 that is "otolaryngology" is an option selected when performing an otolaryngological examination or surgery. The option 344 that is "orthopedic surgery" is an option selected when performing an examination or surgery regarding orthopedic surgery.

The display 301 may display an option other than these options, or the display 301 may display these options together with the option other than these options.

The option regarding the function illustrated in FIG. 7 may be displayed after the option regarding the clinical department as illustrated in FIG. 8 is displayed and the user selects a desired clinical department.

Returning to the description with reference to the flowchart illustrated in FIG. 6, in Step S101, in a case where the function or clinical department is selected by the user on side of the medical apparatus 10, and the selection is accepted, the processing proceeds to Step S102.

In Step S102, the medical apparatus 10 requests the monitoring apparatus 11 to download an application.

For example, the application acquisition section 104 (FIG. 4) transmits, to the monitoring apparatus 11, via the communication control section 105, information regarding the function (clinical department) accepted by the user interface 102, thus requesting the monitoring apparatus 11 to download an application.

Alternatively, the application acquisition section 104 selects, from the function (clinical department) accepted by the user interface 102, an application that is to be downloaded by the application selection section 103 (FIG. 4), and transmits a result of the selection to the monitoring apparatus 11 via the communication control section 105, thus requesting the monitoring apparatus 11 to download the application.

In Step S131, when accepting a request from the medical apparatus 10, the monitoring apparatus 11 selects an application in Step S132. When the communication control section 203 (FIG. 5) in the monitoring apparatus 11 receives the request from the medical apparatus 10, the application managing section 202 (FIG. 5) reads, from the storage section 204, an application corresponding to the request.

For example, in a case where the received request is a request at the time when the option 341 that is "digestive surgery" is selected, the application managing section 202 reads the digestive application 211 from the storage section 204.

In Step S133, the monitoring apparatus 11 transmits the application read from the storage section 204 to the medical apparatus 10 under a control of the communication control section 203.

In Step S103, the medical apparatus 10 receives the application transmitted from the monitoring apparatus 11. Thus, the medical apparatus 10 downloads the application from the monitoring apparatus 11.

The medical apparatus 10 functions as an apparatus that is able to execute processing based on the downloaded application. For example, in a case where the digestive application 211 is downloaded, the medical apparatus 10 functions as an apparatus that performs a digestive examination or surgery.

In addition, for example, in a case where the urological application 212 is downloaded, the medical apparatus 10 functions as an apparatus that performs a urological examination or surgery. In addition, for example, in a case where the orthopedic-surgical application 213 is downloaded, the medical apparatus 10 functions as an apparatus that performs an orthopedic-surgical examination or surgery.

In a case where the medical apparatus 10 is used as a digestive endoscope that performs a digestive examination or surgery on the basis of the digestive application 211, an image in which an object appears red (a color of an organ) is often handled.

Therefore, it is assumed that the digestive application 211 that is intended to allow the medical apparatus 10 to be used as a digestive endoscope is an application intended to set a parameter that enables appropriate image processing of the red object, in other words, to set a parameter for performing image processing that makes the operative site clearly visible, and perform the processing using the parameter.

In a case where the medical apparatus 10 is used as a urological endoscope that performs a urological examination or surgery on the basis of the urological application 212, a rigid scope in the urological endoscope has a small diameter, which is likely to cause a lens distortion.

Therefore, it is assumed that the urological application 212 that is intended to allow the medical apparatus 10 to be used as a urological endoscope is an application intended to perform signal processing that corrects the lens distortion, set a parameter suitable for performing such a correction, and perform the processing using the parameter.

In addition, in a case where the medical apparatus 10 is used as a urological endoscope, there is a case where rotating an image by image processing makes it easier for the surgeon to perform the surgery, etc.

Therefore, it is assumed that the urological application 212 that is intended to allow the medical apparatus to be used as a urological endoscope is an application including a mechanism that performs such image processing as image rotation without an instruction from a surgeon or allows the surgeon to provide an instruction easily.

In a case where the medical apparatus 10 is used as an orthopedic-surgical endoscope that performs an orthopedic-surgical examination or surgery on the basis of the orthopedic-surgical application 213, an image in which an object appears white (a color of a bone) is often handled.

Therefore, it is assumed that the orthopedic-surgical application 213 that is intended to allow the medical apparatus 10 to be used as an orthopedic-surgical endoscope is an application intended to set a parameter that enables appropriate image processing of the white object, in other words, to set a parameter for performing image processing that makes the operative site clearly visual, and perform the processing using the parameter.

Thus, the application downloaded to the medical apparatus 10 enables the medical apparatus 10 to function as a medical apparatus corresponding to various clinical departments. In addition, this also allows the application to be an application that sets a parameter suitable for each clinical department and executes processing using the parameter.

Returning to the description with reference to the flowchart illustrated in FIG. 6, when the medical apparatus 10 receives an application in Step S103, the processing proceeds to Step S104. In Step S104, the application execution section 101 accepts a request to execute the downloaded application. For example, in a case where a user performs a predetermined manipulation, such as manipulating a button to instruct to start an examination, it is determined that a request to execute the application is issued, and the request is accepted.

It is to be noted that it is also possible to omit the processing in Step S104. In other words, upon downloading of the application, the application execution section 101 may start processing based on the application.

In Step S105, the application execution section 101 in the medical apparatus 10 executes the downloaded application. For example, in a case where the digestive application 211 is downloaded, a digestive examination or surgery is started, and image processing, etc. related to the examination or surgery is started.

In Step S106, it is determined whether or not the surgery (examination) is finished. For example, in a case where the surgeon manipulates a button to finish the examination or surgery, in a case where a predetermined period of time has elapsed during which no manipulation is performed or no updating of an image is performed, in a case where the power supply is turned off, etc., it is determined that the surgery (or examination) is finished.

In Step S106, until it is determined that the surgery (or examination) is finished, the processing in Step S106 is repeated, and in a case where it is determined that the surgery (or examination) is finished, the processing proceeds to Step S107.

In Step S107, the downloaded application is deleted from the medical apparatus 10.

Thus, the medical apparatus 10 downloads an application when starting processing, and deletes the application when the processing is finished. Accordingly, when using the medical apparatus 10, it is possible to download and use an application suitable for an intended use.

It is to be noted that in the medical apparatus 10, during a period from when processing starts to when the processing is finished, the medical apparatus 10 and the monitoring device 11 may perform data transfer between each other. For example, the monitoring apparatus 11 may perform a portion of processing that is performed in the medical apparatus 10, the medical apparatus 10 may transmit, as needed, necessary data for performing the processing (for example, image data, observation data, and so on) to the monitoring apparatus 11, and the monitoring apparatus 11 may transmit a result of the processing to the medical apparatus 10.

Thus, in a case of managing an application at the monitoring apparatus 11, in other words, in a case of not causing the medical apparatus 10 to manage an application, it is possible to collectively update the medical apparatuses 10-1 to 10-6.

In other words, updating an application managed by the monitoring apparatus 11, which is, for example, updating (update) of the digestive application 211, the urological application 212, and the orthopedic-surgical application 213 in the example illustrated in FIG. 5, means updating all of the medical apparatuses 10-1 to 10-6 that perform processing using the updated application.

When assuming a case where each of the medical apparatuses 10-1 to 10-6 manages an application separately, it is necessary to perform updating for each of the medical apparatuses 10-1 to 10-6. In such a case, it is obvious that it takes a trouble and time to perform updating, and there is also a possibility of resulting in a state where updating of some of the medical apparatuses 10-1 to 10-6 is forgotten.

According to the present technology, it is possible to save such a trouble and time, and to collectively update all of the medical apparatuses 10.

In addition, when assuming a case of managing an application for each medical apparatus 10, it is necessary to manage any one of the digestive application 211, the urological application 212, and the orthopedic-surgical application 213 or these applications.

In a case of managing an application for any one of the digestive application 211, the urological application 212, and the orthopedic-surgical application 213, it is only possible to perform processing with the managed application, which is likely to prevent an efficient use of the medical apparatus 10.

In addition, in a case of managing the digestive application 211, the urological application 212, and the orthopedic-surgical application 213 for each medical apparatus 10, it is necessary for the medical apparatus 10 to manage a plurality of applications. This is likely to cause an increase in a storage capacity to store the plurality of applications, cause an increase in functionality, etc. to manage and select a desired application from among the plurality of applications, cause a configuration in the medical apparatus 10 to be complicated, and result in an increase in cost and development expenditure.

However, according to the present technology, as described above, no application is managed on the side of the medical apparatus 10, thus making it possible to prevent an increase in storage capacity and an increase in cost and development expenditure.

Processing in Second Embodiment

Figure 9:
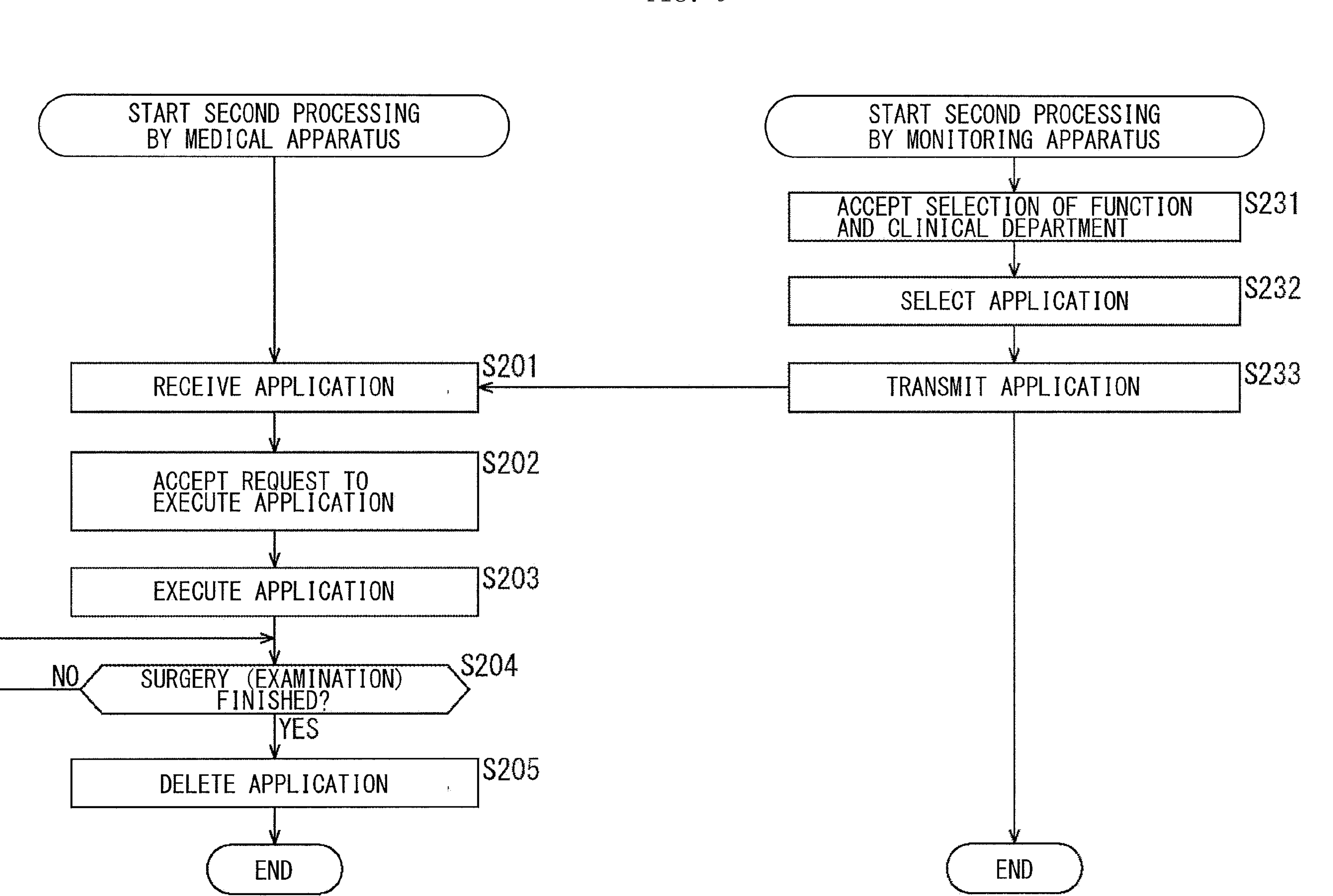
FIG. 9 describes processing by a system in a second embodiment.

FIG. 9 is a flowchart that describes processing by a medical system in a second embodiment. The processing illustrated in FIG. 9 is started after a power supply for a medical apparatus is turned on.

The processing by the medical system in the second embodiment is different from the processing in the first embodiment in that the monitoring apparatus 11 performs a portion of the processing that is performed by the medical apparatus 10 in the medical system in the first embodiment. In the medical system according to the second embodiment, the monitoring apparatus 11 accepts a selection of a function or clinical department for the medical apparatus 10.

In Step S231, the monitoring apparatus 11 accepts a selection of a function and a clinical department for the medical apparatus 10 monitored by the monitoring apparatus 11. It is possible to perform this processing in a manner similar to the processing performed by the medical apparatus 10 in Step S101 in the flowchart illustrated in FIG. 6.

In the second embodiment, as illustrated in FIG. 1, the monitoring apparatus 11 is provided in the monitoring room G, and an observer monitors the operating room A, for example. In addition, the observer performs setting of the medical apparatus 10-1 that is provided in the operating room A. On the basis of this setting, the function or clinical department that corresponds to a surgery (examination) performed using the medical apparatus 10 is selected.

In Step S231, an application corresponding to the function or clinical department that is selected by the monitoring apparatus 11 is selected in Step S232. The processing in Steps S232 and S233 is performed in a manner similar to the Steps S132 and S133 (FIG. 6), and therefore the description thereof is omitted here.

In Step S201, the medical apparatus 10 receives an application transmitted from the monitoring apparatus 11. The medical apparatus 10 may constantly wait for the application to be transmitted from the monitoring apparatus 11, or may accept the application only when the surgeon issues a standby instruction to the medical apparatus 10.

The processing in Steps S201 to S205 after downloading the application on the side of the medical apparatus 10 is performed in a manner similar to the processing in Steps S103 to S107 (FIG. 6) in the first embodiment, and therefore the description thereof is omitted here.

As in the second embodiment, it is possible to set, on side of the monitoring apparatus 11, in other words, using an apparatus other than the medical apparatus 10, an application suitable for the examination or surgery that is desired to be performed by the medical apparatus 10.

In the second embodiment as well, it is possible to achieve an effect similar to the effect in the first embodiment.

Processing in Third Embodiment

FIG. 10 is a flowchart that illustrates processing by a medical system in a third embodiment. The processing based on the flowchart illustrated in FIG. 10 is started after a power supply of a medical apparatus is turned on.

The processing performed by the medical system in the third embodiment is different from the processing in the first embodiment in that a portion of the processing performed by the medical apparatus 10 in the medical system in the first embodiment is performed on the side of the medical apparatus 10 without bothering a surgeon. In the medical system in the third embodiment, the medical apparatus 10 recognizes an apparatus that has been coupled and downloads an application corresponding to a result of the recognition.

In Step S301, the coupled apparatus recognition section 106 in the medical apparatus 10 recognizes the coupled apparatus 131 that has been coupled. In Step S302, on the basis of a result of the recognition, a request to download an application is issued to the monitoring apparatus 11.

For example, the coupled apparatus 131 is a camera head in an endoscopic surgery system (for example, the camera head 23 illustrated in FIGS. 2 and 3). The camera head differs in scope diameter and lens depending on each clinical department, and therefore it is possible to recognize, by the difference, the coupled apparatus 131 that has been coupled. In addition, model number information may be acquired from the coupled apparatus 131 to recognize the coupled apparatus 131 that has been coupled.

A result of the recognition in which the coupled apparatus 131 is recognized by the coupled apparatus recognition section 106 may be transmitted to the monitoring apparatus 11 via the communication control section 105, to cause an application to be selected on the side of the monitoring apparatus 11 on the basis of the result of the received recognition.

Alternatively, on the basis of the result of the recognition in which the coupled apparatus 131 is recognized by the coupled apparatus recognition section 106, the application selection section 103 may select an application and transmit a result of the selection to the monitoring apparatus 11 via the communication control section 105, to cause the application to be selected on the side of the monitoring apparatus 11 on the basis of the received result of the selection.

In Step S302, the medical apparatus 10 transmits, to the side of the monitoring apparatus 11, the result of the recognition from the coupled apparatus recognition section 106 or the result of the selection from the application selection section 103, as a request to download an application.

The processing after the transmission is performed in a manner similar to the first embodiment. In other words, the processing performed in the medical apparatus 10 in Steps S303 to S307 is performed in a manner similar to Steps S103 to S107 (FIG. 6), and therefore the description thereof is omitted. In addition, the processing performed in the monitoring apparatus 11 in Steps S331 to S333 is performed in a manner similar to Steps S131 to S133 (FIG. 6), and therefore the description thereof is omitted.

As in the third embodiment, selecting an application from the apparatus coupled to the medical apparatus 10 makes it possible to set, without bothering a user, an application suitable for the examination or surgery that is desired to be performed in the medical apparatus 10.

In the third embodiment as well, it is possible to achieve an effect similar to the effect in the first embodiment.

It is to be noted that it is naturally possible to perform each of the first, the second, and the third embodiments, but it is also possible to perform the embodiments in combination.

According to the present technology, it is possible to simplify an internal system of the medical apparatus and achieve a reduction in the system cost and development expenditure for the medical apparatus. It is possible to share the medical apparatus to which the present technology is applied among a plurality of clinical departments, thus achieving an efficient use of an operating room and the medical apparatus, a reduction in storage area for the medical apparatus, and a reduction in the number of processes in an installation work for the medical apparatus.

In addition, according to the present technology, it is also possible to provide a medical apparatus to which the present technology is applied in each of a plurality of operating rooms and laboratories, and provide a monitoring apparatus (server) outside the operating room as a shared server. Enabling such a configuration also makes it possible to, when updating a new function, omit an update work for the medical apparatus in each operating room (laboratory) by updating only an application in the server, thus making it possible to reduce the number of processes in a maintenance work for the medical apparatus.

In addition, according to the present technology, there is a case where the medical apparatus and the server achieve, in cooperation with each other, a new function to be updated. For example, in the endoscopic surgery system, it is possible to consider an application in which preprocessing such as compression is performed on an image acquired from the camera head, a result of which is subsequently transmitted to the server, and after the server expands the image again, main processing to extract a characteristic point, etc. is performed using a high-performance processing engine.

When performing such processing, when a person in charge of the maintenance of the medical apparatus only performs updating of the server and forgets to update the medical apparatus, the preprocessing becomes obsolete processing, which is likely to lead to an unfavorable result as a whole. According to the present technology, the server is the only target of updating, it is possible to prevent an occurrence of such an inconvenience.

<Regarding Recording Medium>

It is possible to execute the above-described series of processing by hardware or by software. In a case of executing the series of processing by software, a program included in the software is installed in a computer. Here, the computer includes a computer integrated in dedicated hardware, and includes, for example, a general-purpose personal computer that is able to execute various functions by installing various programs.

Figure 11:
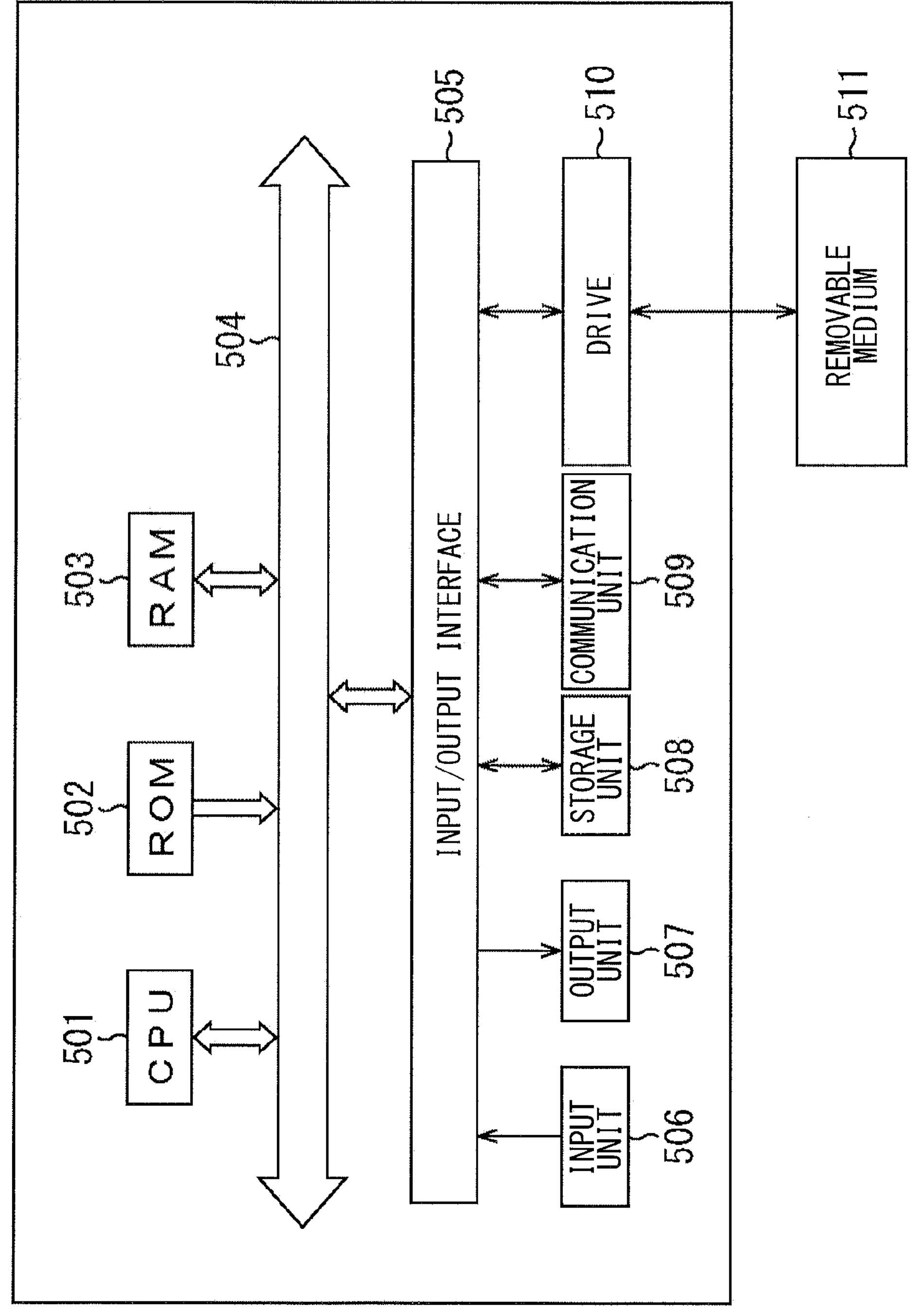
FIG. 11 describes a recording medium.

FIG. 11 is a block diagram that illustrates an example of a configuration of computer hardware that executes the above-described series of processing by a program. In the computer, a CPU (Central Processing Unit) 501, a ROM (Read Only Memory) 502, and a RAM (Random Access Memory) 503 are coupled to one another by a bus 504. To the bus 504, an input/output interface 505 is further coupled. To the input/output interface 505, an input unit 506, an output unit 507, a storage unit 508, a communication unit 509, and a drive 510 are coupled.

The input unit 506 includes a keyboard, a mouse, and a microphone. The output unit 507 includes a display and a speaker. The storage unit 508 includes a hard disk and a non-volatile memory. The communication unit 509 includes a network interface. The drive 510 drives a removable medium 511 such as a magnetic disk, an optical disk, a magneto-optical disk, or a semiconductor memory.

In the computer configured as above, for example, the CPU 501 loads a program stored in the storage unit 508 to the RAM 503 via the input/output interface 505 and the bus 504, and executes the program, thus performing the above-described series of processing.

For example, it is possible to record and provide the program to be executed by the computer (CPU 501) in the removable medium 511 as a package medium or the like. In addition, it is possible to provide the program via a wired or wireless transmission medium such as a local area network, the Internet, or digital satellite broadcasting.

In the computer, it is possible to install a program in the storage unit 508 via the input/output interface 505 by mounting the removable medium 511 on the drive 510. In addition, it is possible to receive the program at the communication unit 509 via the wired or wireless transmission medium, and install the program in the storage unit 508. Alternatively, it is possible to install the program in advance in the ROM 502 or the storage unit 508.

It is to be noted that the program executed by the computer may be a program that causes processing to be performed in chronological order in accordance with an order described in the present specification, or may be a program that causes processing to be performed in parallel or at a necessary timing when a call is made, etc.

In addition, in the present specification, the system represents an entire apparatus that includes a plurality of apparatuses.

It is to be noted that effects described herein are merely illustrative and are not limitative, and may have other effects.

It is to be noted that embodiments according to the present technology are not limited to those described above, and various modifications are possible without departing from the gist of the present technology.

It is to be noted that the present technology may also have the following configurations.

(1)

A surgery system including:

an information processor; and a surgical apparatus, the information processor including a storage section storing an application, and a transmission section transmitting, in response to a request from the surgical apparatus, the application stored in the storage section, and the surgical apparatus including a reception section receiving the application transmitted by the transmission section, and an execution section executing the application received by the reception section.

(2)

The surgery system according to (1), in which the storage section stores an application per clinical department, and the execution section executes the application, to thereby be used as the surgical apparatus having a function suitable for the clinical department.

(3)

The surgery system according to (2), in which the surgical apparatus accepts a selection of the clinical department, and requests the information processor to transmit an application corresponding to the accepted clinical department.

(4)

The surgery system according to (2), in which the information processor accepts a selection of the clinical department, and transmits, to the surgical apparatus, an application corresponding to the accepted clinical department.

(5)

The surgery system according to (2), in which the surgical apparatus recognizes an apparatus that is coupled, and transmits information regarding the recognized apparatus to the information processor, and the information processor transmits, to the surgical apparatus, an application for the clinical department corresponding to the information regarding the apparatus.

(6)

The surgery system according to any one of (1) to (5), in which the surgical apparatus includes a rigid endoscope.

(7)

The surgery system according to any one of (1) to (6), in which the information processor is provided outside an operating room in which the surgical apparatus is disposed.

(8)

A control method, for a surgery system that includes an information processor and a surgical apparatus, the method including:

causing the information processor to store an application per clinical department, and transmit the stored application in response to a request from the surgical apparatus; and causing the surgical apparatus to receive the application transmitted by the information processor, and execute the received application.

(9)

A surgical apparatus, including:

an acquisition section that acquires an application per clinical department from an information processor that stores the application; and an execution section that executes the application acquired by the acquisition section.

(10)

The surgical apparatus according to (9), in which the execution section executes the application, to thereby be used as the surgical apparatus having a function suitable for the clinical department.

(11)

The surgical apparatus according to (9) or (10), in which the surgical apparatus accepts a selection of the clinical department, and requests the information processor to transmit an application corresponding to the accepted clinical department.

(12)

The surgical apparatus according to (9) or (10), in which the surgical apparatus acquires an application corresponding to the accepted clinical department, in the information processor.

(13)

The surgical apparatus according to (9) or (10), further including a coupled apparatus recognition section that recognizes an apparatus that is coupled and acquires information regarding the recognized apparatus, in which the surgical apparatus transmits, to the information processor, the information regarding the apparatus acquired by the coupled apparatus recognition section.

(14)

The surgical apparatus according to any one of (9) to (13), further including an image pickup unit that captures an image of an affected area.

(15)

A control method, including:

acquiring an application per clinical department from an information processor that stores the application; and executing the acquired application to thereby execute processing suitable for the clinical department.

(16)

A program that causes a computer, which controls a medical apparatus, to execute processing, the processing including:

acquiring an application per clinical department from an information processor that stores the application; and executing the acquired application to thereby execute processing suitable for the clinical department.

REFERENCE NUMERALS LIST

10 medical apparatus
11 monitoring apparatus
101 application execution section
102 user interface
103 application selection section
104 application acquisition section
105 communication control section
106 coupled apparatus recognition section
107 storage unit
111 common application
131 coupled apparatus
201 user interface 202 application managing section
203 communication control section
204 storage unit
211 digestive application
212 urological application
213 orthopedic-surgical application
301 display
321 to 324 option
341 to 344 option

The invention claimed is:

1. An endoscopic system comprising:
an information processor; and
a endoscope control apparatus, wherein the endoscope control apparatus is configured to be coupled to different endoscopic apparatuses, to recognize a coupled endoscopic apparatus among the different endoscopic apparatuses, and transmit information regarding the coupled endoscopic apparatus to the information processor, and
the information processor is configured to transmit, to the endoscope control apparatus, an endoscopic image processing application corresponding to the information regarding the recognized coupled endoscopic apparatus to the endoscope control apparatus,
the information processor including
a memory storing a plurality of different endoscopic image processing applications to operate corresponding different endoscopic apparatuses, and
transmission circuitry configured to transmit, in response to a request from the endoscope control apparatus, the application stored in the memory based on the information regarding the coupled endoscopic apparatus, and
the endoscope control apparatus including processing circuitry configured to
receive the endoscopic image processing application transmitted by the transmission circuitry, and
execute the endoscopic image processing application, to thereby be used as the endoscope control apparatus having a function suitable for the recognized coupled endoscopic apparatus.

2. The endoscopic system according to claim 1, wherein the memory is configured to store an endoscopic image processing application per clinical department, and
the processing circuitry is configured to execute the image processing application, to thereby be used as the endoscopic apparatus having a function suitable for the clinical department.

3. The endoscopic system according to claim 2, wherein the endoscope control apparatus accepts a selection of the clinical department, and requests the information processor to transmit an application corresponding to the accepted clinical department.

4. The endoscopic system according to claim 2, wherein the information processor accepts a selection of the clinical department, and transmits, to the endoscope control apparatus, an application corresponding to the accepted clinical department.

5. The endoscopic system according to claim 2, wherein the endoscope control apparatus recognizes an apparatus that is coupled, and transmits information regarding the recognized apparatus to the information processor, and
the information processor transmits, to the endoscope control apparatus, an application for the clinical department corresponding to the information regarding the apparatus.

6. The endoscopic system according to claim 1, wherein the endoscope control apparatus includes a rigid endoscope.

7. The endoscopic system according to claim 1, wherein the information processor is provided outside an room in which the endoscopic apparatus is disposed.

8. The endoscopic system according to claim 1, wherein the endoscope control apparatus is configured to delete the received endoscopic image processing application when an operation of the recognized coupled endoscopic apparatus is finished.

9. The endoscopic system according to claim 1, wherein the endoscopic image processing application performs an image color adjustment process based on a red-color component of an organ.

10. The endoscopic system according to claim 1, wherein the coupled endoscopic apparatus is a camera head, and the information regarding the recognized coupled endoscopic apparatus includes at least one of a scope diameter or a lens type of the camera head.

11. The endoscopic system according to claim 1, wherein the information processor is a shared server provided outside of a room in which the endoscope control apparatus is disposed and is configured to collectively update applications for a plurality of rooms.

12. The endoscopic system according to claim 1, wherein the coupled endoscopic apparatus includes a photoelectric conversion module and is configured to transmit image signals to the endoscope control apparatus via optical communication.

13. The endoscopic system according to claim 1, wherein the endoscopic image processing application configures the endoscope control apparatus to perform preprocessing on image data acquired from the coupled endoscopic apparatus and transmit the preprocessed data to the information processor for main processing.

14. The endoscopic system according to claim 1, wherein the endoscopic image processing application configures the endoscope control apparatus for special light observation including at least one of narrow band imaging or fluorescence observation.

15. The endoscopic system according to claim 1, wherein the endoscope control apparatus is configured to automatically trigger the request for the endoscopic image processing application from the information processor immediately upon recognizing the coupled endoscopic apparatus.

16. The endoscopic system according to claim 1, wherein the processing circuitry is configured to execute the received endoscopic image processing application by dynamically loading a library corresponding to the application.

17. The endoscopic system according to claim 2, wherein the memory of the endoscope control apparatus stores a common application providing functions independent of a clinical department, and the processing circuitry is configured to execute the endoscopic image processing application in combination with the common application.

18. The endoscopic system according to claim 1, wherein the endoscope control apparatus recognizes the coupled endoscopic apparatus by reading a unique identification code stored in a memory within a connector of the coupled endoscopic apparatus.

19. A method for an endoscopic system, comprising:
recognizing, by a endoscope control apparatus, a coupled endoscopic apparatus among different endoscopic apparatuses;
transmitting, from the endoscope control apparatus to an information processor, information regarding the recognized coupled endoscopic apparatus;

transmitting, from the information processor to the endoscope control apparatus, an endoscopic image processing application corresponding to the information regarding the recognized coupled endoscopic apparatus;

receiving, by the endoscope control apparatus, the transmitted endoscopic image processing application; and executing, by the endoscope control apparatus, the received endoscopic image processing application to thereby perform an image processing function suitable for the recognized coupled endoscopic apparatus.

20. A non-transitory computer-readable medium storing instructions which, when executed by a processor of an endoscope control apparatus, cause the endoscope control apparatus to perform operations comprising:

recognizing a coupled endoscopic apparatus among different endoscopic apparatuses; transmitting, to an information processor, information regarding the recognized coupled endoscopic apparatus;

receiving, from the information processor, an endoscopic image processing application corresponding to the information regarding the recognized coupled endoscopic apparatus; and executing the received endoscopic image processing application to thereby perform an image processing function suitable for the recognized coupled endoscopic apparatus.

* * * * *